United States Patent
Ukai

(10) Patent No.: US 7,600,409 B2
(45) Date of Patent: Oct. 13, 2009

(54) FAILURE DIAGNOSTIC DEVICE FOR ACCELERATION SENSOR, ELECTRONIC DEVICE EQUIPPED WITH FAILURE DIAGNOSTIC DEVICE, FAILURE DIAGNOSTIC SYSTEM, AND FAILURE DIAGNOSTIC METHOD

(75) Inventor: Akihiro Ukai, Osakasayama (JP)

(73) Assignee: Konica Minolta Sensing, Inc., Sakai-shi (JP)

( * ) Notice: Subject to any disclaimer, the term of this patent is extended or adjusted under 35 U.S.C. 154(b) by 475 days.

(21) Appl. No.: 11/489,871

(22) Filed: Jul. 20, 2006

(65) Prior Publication Data

US 2007/0028664 A1 Feb. 8, 2007

(30) Foreign Application Priority Data

Aug. 3, 2005 (JP) ............................. 2005-225974

(51) Int. Cl.
*G01P 21/00* (2006.01)
(52) U.S. Cl. ........................................................ 73/1.39
(58) Field of Classification Search ................. None
See application file for complete search history.

(56) References Cited

U.S. PATENT DOCUMENTS

| 6,988,409 B2 * | 1/2006 | Furuichi | 73/514.32 |
| 2005/0131602 A1 * | 6/2005 | Souda | 701/34 |

FOREIGN PATENT DOCUMENTS

JP 11-211751 A 8/1999

* cited by examiner

*Primary Examiner*—Robert R Raevis
(74) *Attorney, Agent, or Firm*—Sidley Austin LLP

(57) ABSTRACT

A failure diagnostic device for diagnosing whether a failure has occurred in an acceleration sensor to be loaded in an electronic device such as a living body information measurement device of acquiring data concerning e.g. living body information includes: an acceleration calculator for calculating an acceleration applied to the electronic device based on an output from the acceleration sensor; and a first judger for judging whether the electronic device is in a stationary state based on a judgment as to whether an output value from the acceleration calculator lies within a predetermined range for a predetermined duration.

17 Claims, 14 Drawing Sheets

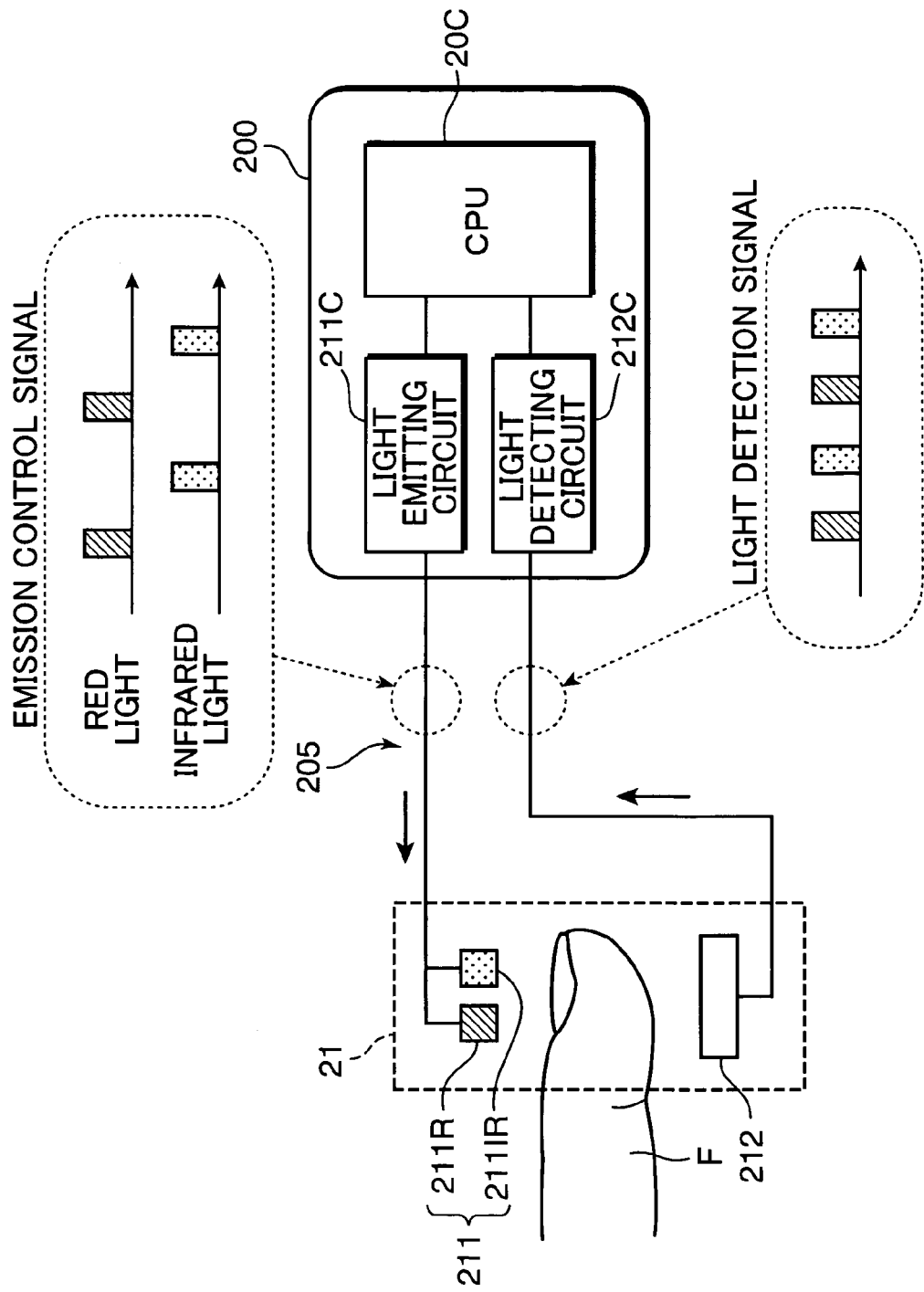

FAILURE DIAGNOSTIC DEVICE FOR ACCELERATION SENSOR, ELECTRONIC DEVICE EQUIPPED WITH FAILURE DIAGNOSTIC DEVICE, FAILURE DIAGNOSTIC SYSTEM, AND FAILURE DIAGNOSTIC METHOD

This application is based on Japanese Patent Application No. 2005-225974 filed on Aug. 3, 2005, the contents of which are hereby incorporated by reference.

BACKGROUND OF THE INVENTION

1. Field of the Invention

The present invention relates to a failure diagnostic device for diagnosing whether a failure has occurred in an acceleration sensor, an electronic device equipped with the failure diagnostic device, a failure diagnostic system, and a failure diagnostic method.

2. Description of the Related Art

An acceleration sensor is loaded in electronic devices of various types. An output from the acceleration sensor is widely used for control of the electronic devices, detection of phenomena such as earthquake behavior or exercise intensity of a living body, and so on.

In the case where the acceleration sensor is loaded specifically in a portable electronic device, a large impact may likely be applied to the electronic device, if the electronic device is inadvertently dropped, for instance. After the impact over a rated value is applied to the acceleration sensor loaded in the electronic device, the acceleration sensor may cause an output value error, which may obstruct output of a normal output value.

If a user of the electronic device is kept being uninformed of abnormality of the acceleration sensor despite of the sensor abnormality, measurement or a like operation is performed under a condition that the user is unaware of the sensor abnormality. As a result, it may be unavoidable that erroneous control or erroneous phenomena detection is carried out by the electronic device based on the erroneous measurement data.

Japanese Unexamined Patent Publication No. 11-211751 discloses an acceleration detecting device, as a technology relating to failure detection of an acceleration sensor. The acceleration detecting device includes a pair of acceleration sensors, and is so constructed that sensitivity axes of the respective acceleration sensors are inclined relative to a horizontal axis, and outputs i.e. vectors from the respective acceleration sensors are distributed in a horizontal direction and a vertical direction in accordance with the inclined angles of the sensitivity axes. The sum i.e. a composite vector of the outputs from the respective acceleration sensors in the horizontal direction is calculated as a horizontal acceleration, and the sum of the outputs from the respective acceleration sensors in the vertical direction is calculated as a vertical acceleration. The acceleration detecting device detects whether a failure has occurred in the acceleration sensors based on the horizontal acceleration and the vertical acceleration. The publication discloses providing a computation circuit including amplifiers and adders of realizing computations corresponding to the vector distribution and the vector synthesis so as to obtain the horizontal acceleration and the vertical acceleration.

There is also known use of a reference sensor for detecting a failure of an acceleration sensor, in addition to the above publication.

The arrangement disclosed in the publication has the two acceleration sensors to judge whether a failure has occurred in the acceleration sensors, which increases the cost and the size of the acceleration detecting device. Also, the latter technology of using the reference sensor to detect whether a failure has occurred in the acceleration sensor needs another sensor i.e. the reference sensor in addition to the acceleration sensor for failure detection. Therefore, the latter technology has room for improvement on cost reduction and miniaturization of the acceleration detecting device, as well as the arrangement disclosed in the publication.

SUMMARY OF THE INVENTION

In view of the above, an object of the invention is to provide a failure diagnostic device that enables to detect whether a failure has occurred in an acceleration sensor, while avoiding or suppressing cost increase or size increase of the failure diagnostic device, as well as an electronic device equipped with the failure diagnostic device, a failure diagnostic system, and a failure diagnostic method.

An aspect of the invention to attain the above object is directed to a failure diagnostic device for diagnosing whether a failure has occurred in an acceleration sensor to be loaded in an electronic device. The failure diagnostic device comprises: an acceleration calculator for calculating an acceleration applied to the electronic device based on an output from the acceleration sensor; and a first judger for judging whether the electronic device is in a stationary state based on a judgment as to whether an output value from the acceleration calculator lies in a predetermine range for a predetermined duration.

Another aspect of the invention is directed to an electronic device comprising: an acceleration sensor; a failure diagnostic device for diagnosing whether a failure has occurred in the acceleration sensor; and a detector for detecting a movement and/or a tilt of an object to which the electronic device is mounted using an output from the acceleration sensor, wherein the failure diagnostic device includes: an acceleration sensor for calculating an acceleration applied to the electronic device based on the output from the acceleration sensor; and a first judger for judging whether the electronic device is in a stationary state based on a judgment as to whether an output value from the acceleration calculator lies within a predetermined range for a predetermined duration.

In the failure diagnostic device or the electronic device, a judgment is made as to whether a failure has occurred in the acceleration sensor using the output from the acceleration sensor, which is an object for failure diagnosis. This eliminates the need of providing plural acceleration sensors, as required in the conventional art, or providing a reference sensor in addition to the acceleration sensor, which contributes to cost reduction and miniaturization of the electronic device.

These and other objects, features and advantages of the present invention will become more apparent upon reading of the following detailed description along with the accompanying drawings.

BRIEF DESCRIPTION OF THE DRAWINGS

FIG. 3 is a circuit diagram schematically showing a circuit configuration of the pulse oximeter.

FIGS. 4A through 4C are diagrams showing a three-axis acceleration sensor using a piezoresistor, as an example of a three-axis acceleration sensor, wherein FIG. 4A is a perspective view, FIG. 4B is a top plan view, and FIG. 4C is a cross-sectional view taken along the line IVC-IVC in FIG. 4B.

DETAILED DESCRIPTION OF THE PREFERRED EMBODIMENTS

Figure 1:
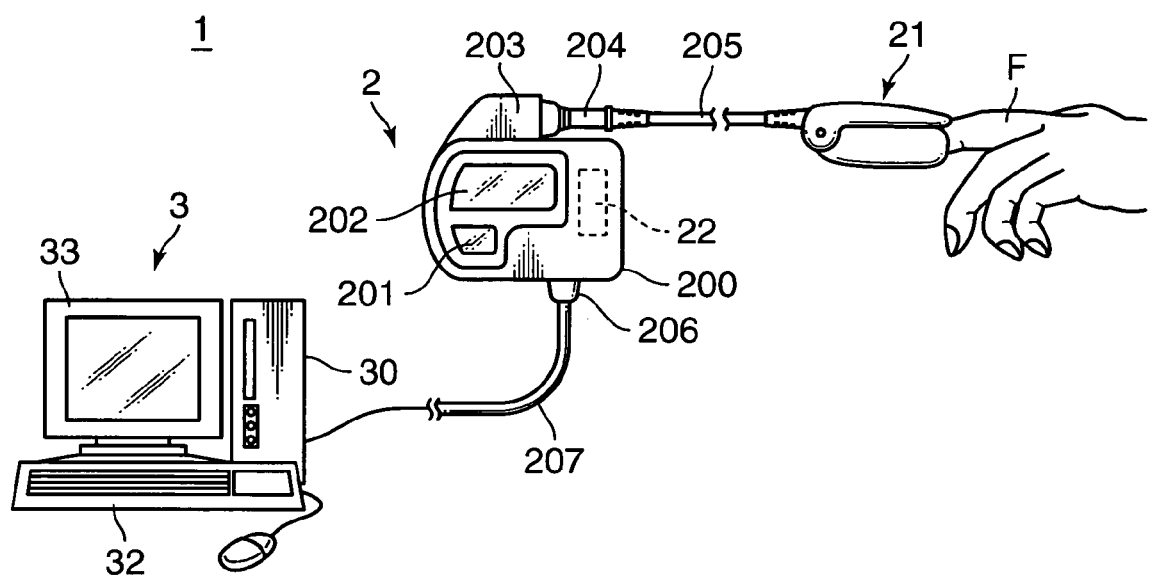
FIG. 1 is a diagram showing an example of a living body information measurement system to which an embodiment of the invention is applied.

In the following, a preferred embodiment of the invention is described referring to the drawings.

FIG. 1 is a diagram showing an example of a living body information measurement system 1 to which the embodiment of the invention is applied. The living body information measurement system 1 includes a pulse oximeter 2 capable of concurrently measuring a blood oxygen saturation and a body tilt angle of a subject, and storing the measurement data, a personal computer (PC) 3, as a data processor, which is operative to read the measurement data stored in the pulse oximeter 2, concerning the blood oxygen saturation and the body tilt angle, for analysis of a certain physiological condition of the subject, and a USB cable 207 for communicatively connecting the pulse oximeter 2 and the PC 3 when needed.

The pulse oximeter 2 includes an oximeter body 200 as an electronic device, and a probe 21. The oximeter body 200 and the probe 21 are electrically connected by a probe cable 205 equipped with a connector 204. The oximeter body 200 externally includes a power switch 201, an oximeter display 202 with a liquid crystal display or the like, a connector section 203 for connecting the probe cable 205, and a connector section 206 for connecting the USB cable 207. Also, the oximeter body 200 internally includes a memory, a microprocessor as a CPU, and a power battery, all of which are not illustrated, in addition to a three-axis acceleration sensor 22.

The probe 21 has a paper-clip like shape capable of securely holding a finger F of the subject to measure the blood oxygen saturation of the subject. Specifically, the probe 21 has a pair of holding pieces which are openably jointed to each other so that the probe 21 can securely hold the finger F with a biasing force of a spring or a like member. As will be described later, a light emitter 211 is provided on one of the holding pieces, and a light detector 212 is provided on the other thereof (see FIG. 3).

Figure 2:
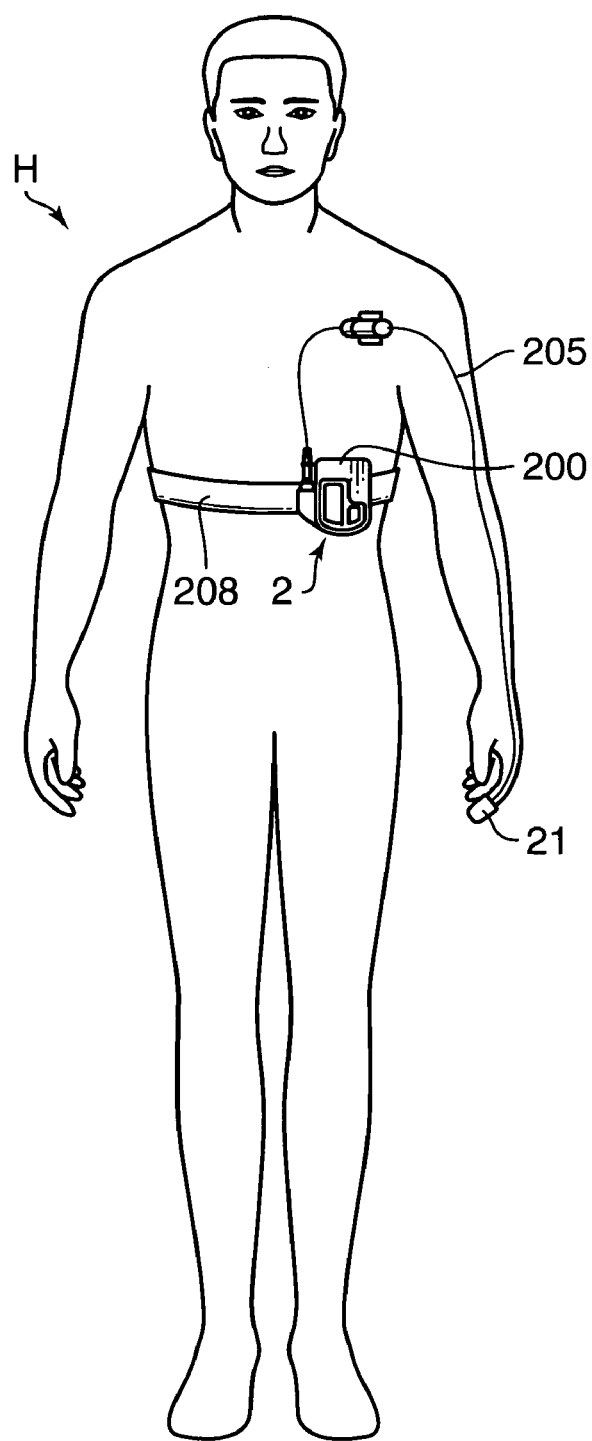
FIG. 2 is a diagram showing a mounted state of a pulse oximeter on a subject.

The oximeter body 200 and the probe 21 are detachably attached to a subject H in the manner as shown in FIG. 2, for instance, in measurement. Specifically, a fastening belt 208 is wound around a body portion of the subject H so that the oximeter body 200 is secured to a body trunk portion of the subject H with use of the fastening belt 208. Also, the probe 21 is fixedly attached to the finger F of the subject H for measurement. Thereafter, the oximeter main body 200 and the probe 21 are connected to each other by the probe cable 205. At the time of measurement, i.e., during sleep of the subject H, the USB cable 207 is not connected to the oximeter body 200. The USB cable 207 is connected to the PC 3 after the measurement is completed to read out the measurement data from the pulse oximeter 2.

Figure 14:
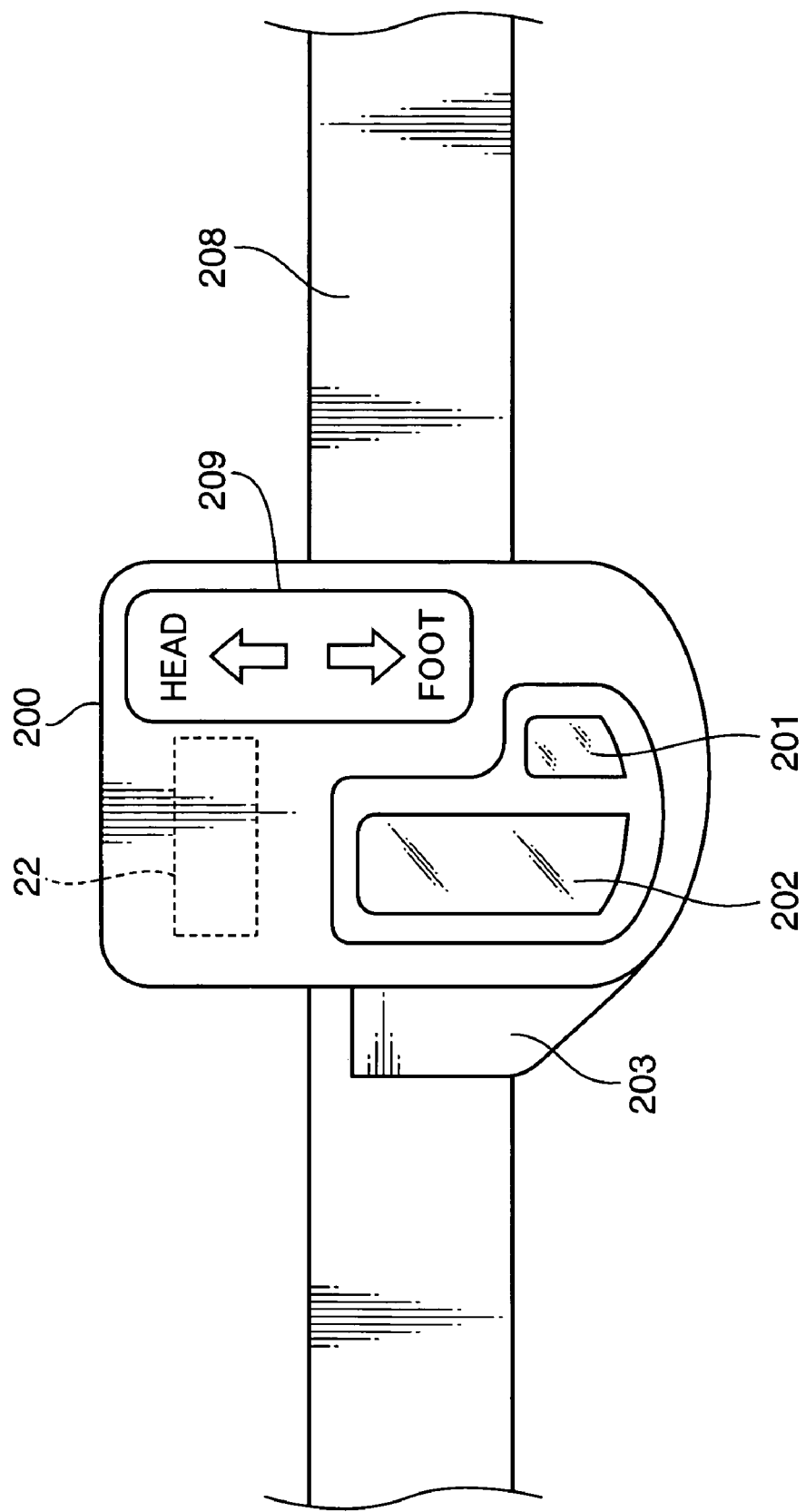
FIG. 14 is a plan view showing the pulse oximeter equipped with a direction guide.

It is desirable to provide a direction guide 209 on an outer surface of a casing of the oximeter body 200 to display a direction in which the pulse oximeter 2 should normally be attached to the subject H, as shown in FIG. 14, so that outputs from the three-axis acceleration sensor 22 with respect to respective axes thereof are accurately obtained as designed in view of a fact that the three-axis acceleration sensor 22 is provided in the oximeter body 200. Specifically, if the pulse oximeter 2 is inadvertently attached to the subject's body in a direction different from the direction corresponding to the designed axial output of the three-axis acceleration sensor 22, for instance, if the pulse oximeter 2 is attached upside down, plus and minus of X-axis and Y-axis outputs are inverted with respect to the body position of the subject H. In this case, for instance, if the subject rolls over in a rightward direction, such a body position change is misjudged as rolling over in a leftward direction.

In view of this, as shown in FIG. 14, the direction guide 209 is provided on the surface of the casing of the oximeter body 200, wherein "HEAD" and "FOOT" are indicated with arrows to clearly notify a user including the subject H and a medical staff of the direction in which the pulse oximeter 22 should normally be attached to the subject H. This enables to prevent erroneous measurement as described above.

Referring back to FIG. 1, the 3 includes a PC main body 30 i.e. a hard disk device, an operation unit 32 having a keyboard and the like, and a display unit 33 having a cathode ray tube (CRT) display or a liquid crystal display.

FIG. 3 is a diagram schematically showing a circuit configuration of the probe 21 and the oximeter body 200 connected thereto. The probe 21 includes the light emitter 211 and the light detector 212. The light emitter 211 has semiconductor light emitting devices for emitting light of two different wavelengths $\lambda 1$, $\lambda 2$, respectively. For instance, one of the semiconductor light emitting devices is a red LED 211R for emitting red LED light of the wavelength $\lambda 1$ in a red wavelength range, and the other one thereof is an infrared LED 211IR for emitting infrared LED light of the wavelength $\lambda 2$ in an infrared wavelength range. The light detector 212 has a photoelectric conversion device for generating an electric current in accordance with an intensity of light emitted from the light emitter 211. An example of the photoelectric conversion device is a silicon photo diode having photosensitivity to at least the wavelengths λ1 and λ2.

As shown in FIG. 3, the light emitter 211 and the light detector 212 are juxtaposed with respect to the finger F for measurement i.e. living tissue from which the blood oxygen saturation is to be measured. For instance, on the tip of the finger F where a pulse beat of the arterial blood is easily detected optically, the light emitter 211 is arranged adjacent the nail portion of the finger tip, and the light detector 212 is arranged adjacent the ball portion of the finger tip. In an actual measurement, fixedly holding the finger F by the probe 21 enables to dispose the light emitter 211 and the light detector 212 at the aforementioned positions. Alternatively, a medicated tape such as a surgical tape or a first-aid adhesive tape may be used to securely position the light emitter 211 and the light detector 212 relative to the finger F. By the above attachment, the light of the wavelengths λ1, λ2 which has passed through the finger F is detected by the light detector 212.

The light emitter 211 and the light detector 212 are respectively connected to a light emitting circuit 211C and a light detecting circuit 212C. The light emitting circuit 211C and the light detecting circuit 212C are provided in the oximeter body 200. The light emitter 211 and the light detector 212 are electrically connected to the light emitting circuit 211C and the light detecting circuit 212C, respectively, by the probe cable 205.

An operation of the light emitting circuit 211C is controlled by a microprocessor 20C so that a specified emission control signal is issued to the red LED 211R and to the infrared LED 211IR of the light emitter 211. In response to issuance of the emission control signal to the red LED 211R and to the infrared LED 211IR, for instance, the red LED 211R and the infrared LED 211IR are alternately driven, and red light and infrared light are alternately emitted. Also, the light detecting circuit 212C is controlled in synchronism with the emission of the light emitter 211 by the microprocessor 20C to generate an electric current signal i.e. a pulse signal, which is obtained by photoelectrical conversion of the received light in accordance with the received light intensity.

Oxygen is transported by oxidation/reduction of hemoglobin in the blood. The hemoglobin has such optical characteristics that oxidation of hemoglobin decreases absorption of red light and increases absorption of infrared light, and, conversely, reduction of hemoglobin increases absorption of red light and decreases absorption of infrared light. Therefore, it is possible to obtain a blood oxygen saturation i.e. an arterial blood oxygen saturation by measuring variations in transmitted light amounts of the red light and the infrared light, which are detected by the light detecting circuit 212C, by utilizing the optical characteristics.

Figure 4A:
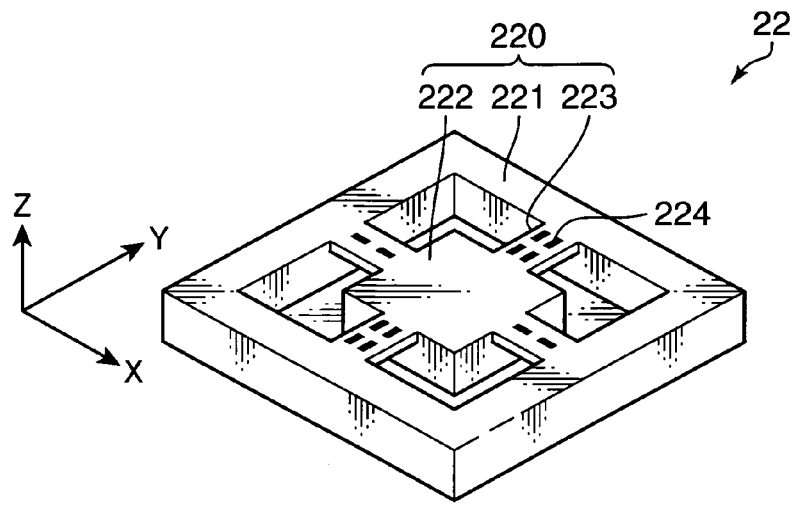
Figure 4B:
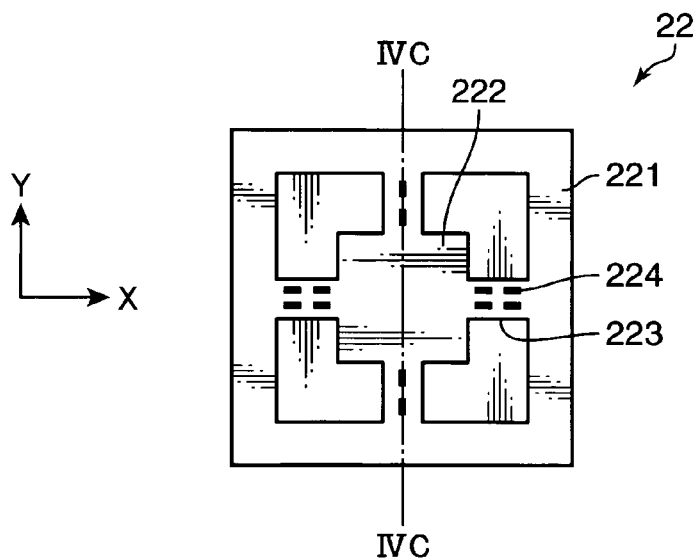
Figure 4C:
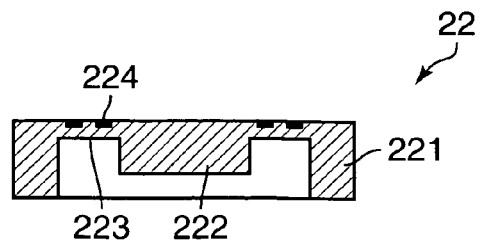

In this section, the three-axis acceleration sensor 22 provided in the oximeter body 200 is described. FIGS. 4A through 4C are diagrams showing a three-axis acceleration sensor using a piezoresistor, as an example of the three-axis acceleration sensor. FIG. 4A is a perspective view of the three-axis acceleration sensor, FIG. 4B is a top plan view thereof, and FIG. 4C is a cross-sectional view taken along the line IVC-IVC in FIG. 4B. The three-axis acceleration sensor 22 is constructed utilizing a piezoresistive effect that application of a mechanical external force to an object composed of a semiconductor material having a piezo effect causes crystal lattice distortion in the object, and varies the number of carriers or carrier moving degree in the object, which causes a change in resistance of the object.

The three-axis acceleration sensor 22 includes a sensor body 220 and twelve piezoresistive devices 224. The sensor body 220 has a four-sided frame-like support 221 formed by dry-etching a base material such as silicon, a weight portion 222 disposed in the middle of the support 221, and thin beam portions 223 each for connecting a corresponding side portion of the support 221 to the weight portion 222. The twelve piezoresistive devices 224 are attached to the beam portions 223, as shown in FIG. 4A, for instance. When the weight portion 222 is vibrated by application of acceleration, the beam portions 223 are deformed, and a stress is applied to the piezoresistive devices 224.

Specifically, when an external force is exerted to the three-axis acceleration sensor 22, a tilting force is exerted on the oximeter body 200. As a result, the weight portion 222 is deformed about X-axis, Y-axis, or Z-axis (see FIG. 4A) depending on the tilting direction of the oximeter body 200, thereby deforming the beam portions 223. Then, a stress is applied to the piezoresistive devices 224 depending on the degree of the deformation of the beam portions 223, and, as a result, the resistances of the piezoresistive devices 224 are varied depending on the application of the stress. Thus, a tilt angle of the oximeter body 200 i.e. the body angle of the subject is detected by detecting variations in resistance of the piezoresistive devices 224, which are extracted as signals proportional to acceleration.

The acceleration-proportional signals regarding the piezoresistive devices 224 can be detected by using a Wheatstone bridge circuit comprising four piezoresistive devices 224 each for the X-axis, Y-axis, and Z-axis, namely, using the twelve piezoresistive devices 224 in total, and by detecting respective variations in resistance resulting from application of stress to the piezoelectric devices 224, as a voltage change.

Figure 5A:
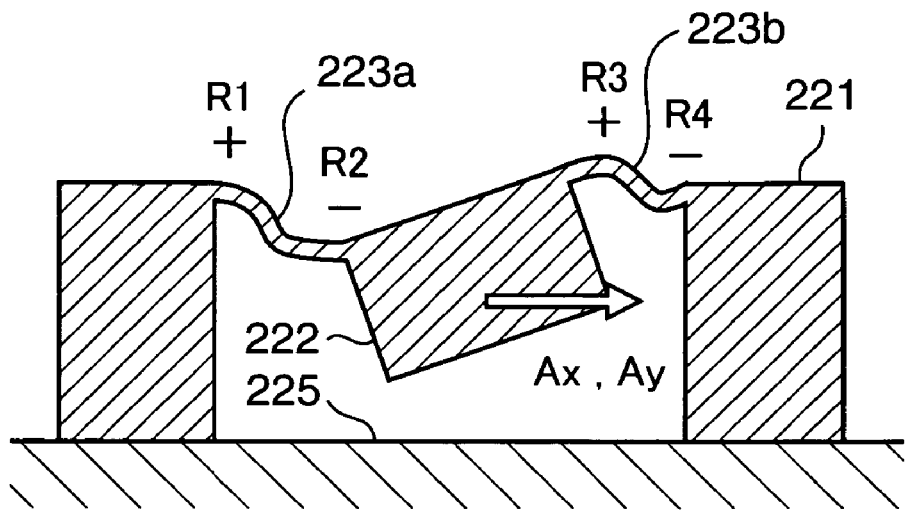
FIG. 5A is a diagram schematically showing a beam model deformed in X-axis direction and Y-axis direction.
Figure 5B:
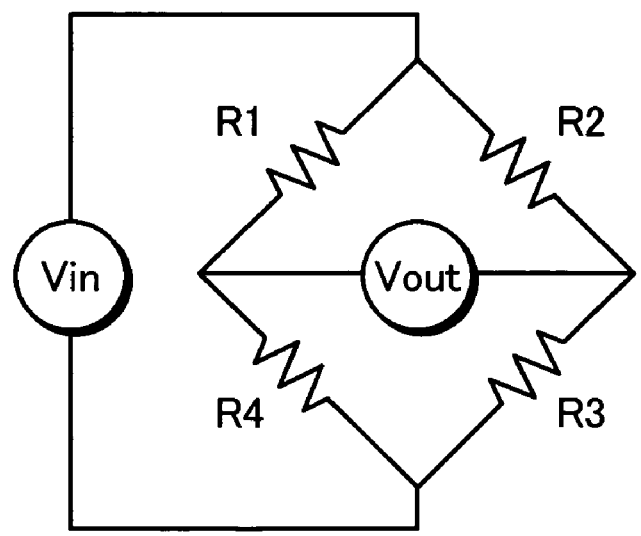
FIG. 5B is a circuit diagram schematically showing a bridge circuit for detecting a voltage variation representing the deformation of the beam model shown in FIG. 5A.

FIG. 5A is a diagram schematically showing deformation of the beam portions 223 i.e. beam portions 22a and 223b in X-axis direction and Y-axis direction, i.e., rotational deformation of the beam portions 223 about the X-axis and the Y-axis. FIG. 5B is a circuit diagram schematically showing a bridge circuit for detecting a voltage change corresponding to the deformation. In FIGS. 5A, 5B, and FIGS. 6A and 6B, which will be described later, symbols R1, R2, R3, and R4 represent four piezoresistive devices 224 in association with one of the X-, Y-, and Z-axes, respectively.

As shown by a deformed beam model in FIG. 5A, when acceleration is applied to the acceleration sensor 22 in the X-axis direction and in the Y-axis direction, a tensile stress is applied to the outer piezoresistive device R1 on the beam portion 223a, with the result that the resistance of the piezoresistive device R1 is increased, and a compressive stress is applied to the inner piezoresistive device R2 on the beam portion 223a, with the result that the resistance of the piezoresistive device R2 is decreased. On the other hand, a tensile stress is applied to the inner piezoresistive device R3 on the beam portion 223b, with the result that the resistance of the piezoresistive device R3 is increased, and a compressive stress is applied to the outer piezoresistive device R4 on the beam portion 223b, with the result that the resistance of the piezoresistive device R4 is decreased. In other words, counteractive resistance variations occur between the piezoresistive devices R1 and R2, and between the piezoresistive devices R3 and R4. Accordingly, in the case where a bridge circuit as shown in FIG. 5B is fabricated, and a constant voltage Vin is applied to the bridge circuit with respect to the X-axis or the Y-axis, an output voltage Vout can be obtained by implementing the equation (2).

$$Vout = \{R4/(R1+R4) - R3/(R2+R3)\} Vin \qquad (2)$$

Figure 6A:
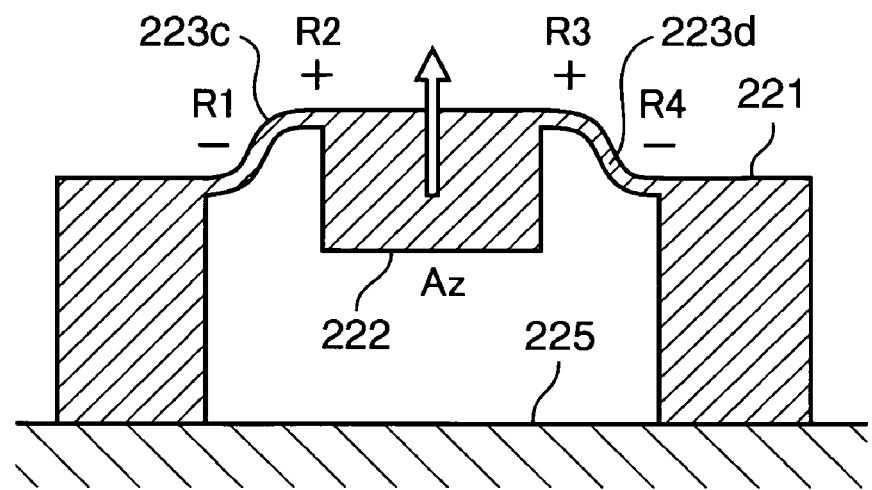
FIG. 6A is a diagram schematically showing a beam model deformed in Z-axis direction.
Figure 6B:
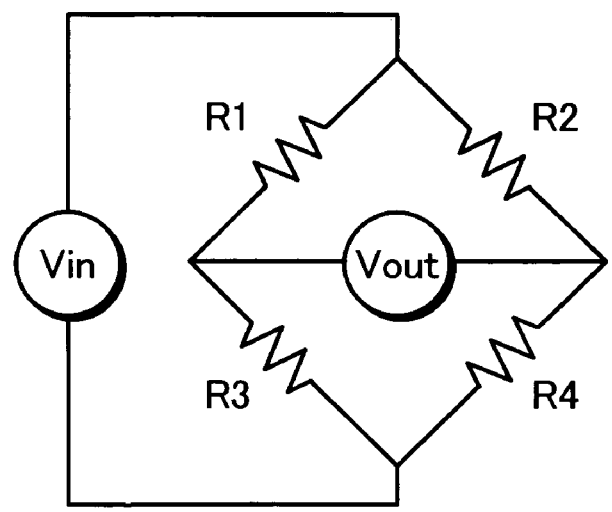
FIG. 6B is a circuit diagram schematically showing a bridge circuit for detecting a voltage variation representing the deformation of the beam model shown in FIG. 6A.

FIG. 6A is a diagram schematically showing deformation of the beam portions 223 or beam portions 223c and 223d in Z-axis direction, i.e., vertical deformation of the beam portions 223 in the Z-axis. FIG. 6B is a circuit diagram schematically showing a bridge circuit for detecting a voltage change corresponding to the deformation.

The weight portion 222 deforms vertically in response to receiving an acceleration in the Z-axis direction. For instance, as shown by a deformed beam model in FIG. 6A, in the case where the weight portion 222 is deformed upwardly, a compressive stress is applied to the outer piezoresistive device R1 on the beam portion 223c, with the result that the resistance of the piezoresistive device R1 is decreased, and a tensile stress is applied to the inner piezoresistive device R2 on the beam portion 223c, with the result that the resistance of the piezoresistive device R2 is increased. On the other hand, a tensile stress is applied to the inner piezoresistive device R3 on the beam portion 223d, with the result that the resistance of the piezoresistive device R3 is increased, and a compressive stress is applied to the outer piezoresistive device R4 on the beam portion 223d, with the result that the resistance of the piezoresistive device R4 is decreased. In other words, counteractive resistance variations occur between the piezoresistive devices R1 and R2, and between the piezoresistive devices R3 and R4. Accordingly, in the case where a bridge circuit as shown in FIG. 6B is fabricated, and a constant voltage Vin is applied to the bridge circuit with respect to the Z-axis, an output voltage Vout can be obtained by implementing the equation (3).

$$V\text{out}=\{R3/(R1+R3)-R4/(R2\times R4)\}V\text{in} \quad (3)$$

The above describes a basic operation principle as to how the acceleration applied to the oximeter body 200 is detected by the three-axis acceleration sensor 22.

Next, a principle is described as to how a tilt angle of the oximeter body 200 i.e. the subject H is detected with use of the three-axis acceleration sensor 22. The acceleration sensor 22 is an inertial sensor for measuring a velocity component in input axis direction or sensitivity axis direction i.e. the X-axis direction, the Y-axis direction, and the Z-axis direction shown in FIG. 4A, wherein the velocity component is obtained by subtracting a gravitational acceleration "G" from a moment acceleration "m". Specifically, the velocity component i.e. acceleration "E" detected by the acceleration sensor 22 is expressed by the equation (4).

$$E=m-G \quad (4)$$

Here, let it be assumed that the acceleration sensor 22 is stationary on the ground i.e. m=0, and the gravitational acceleration "G" along a vertical axis is "1G". Then, in the case where the direction of the sensitivity axis coincides with the upwardly extending direction of the vertical axis, the gravitational acceleration "G" is "+1G", and in the case where the sensitivity axis is tilted by angle θ with respect to the vertical axis, the gravitational acceleration "G" equals "+1G" multiplied by cosθ.

Utilizing the above idea derives angles of the X-axis, the Y-axis, and the Z-axis of the acceleration sensor 22 with respect to the vertical axis based on gravitational accelerations with respect to the three axes, i.e., the X-, Y-, and Z-axes of the acceleration sensor 22.

Figure 7:
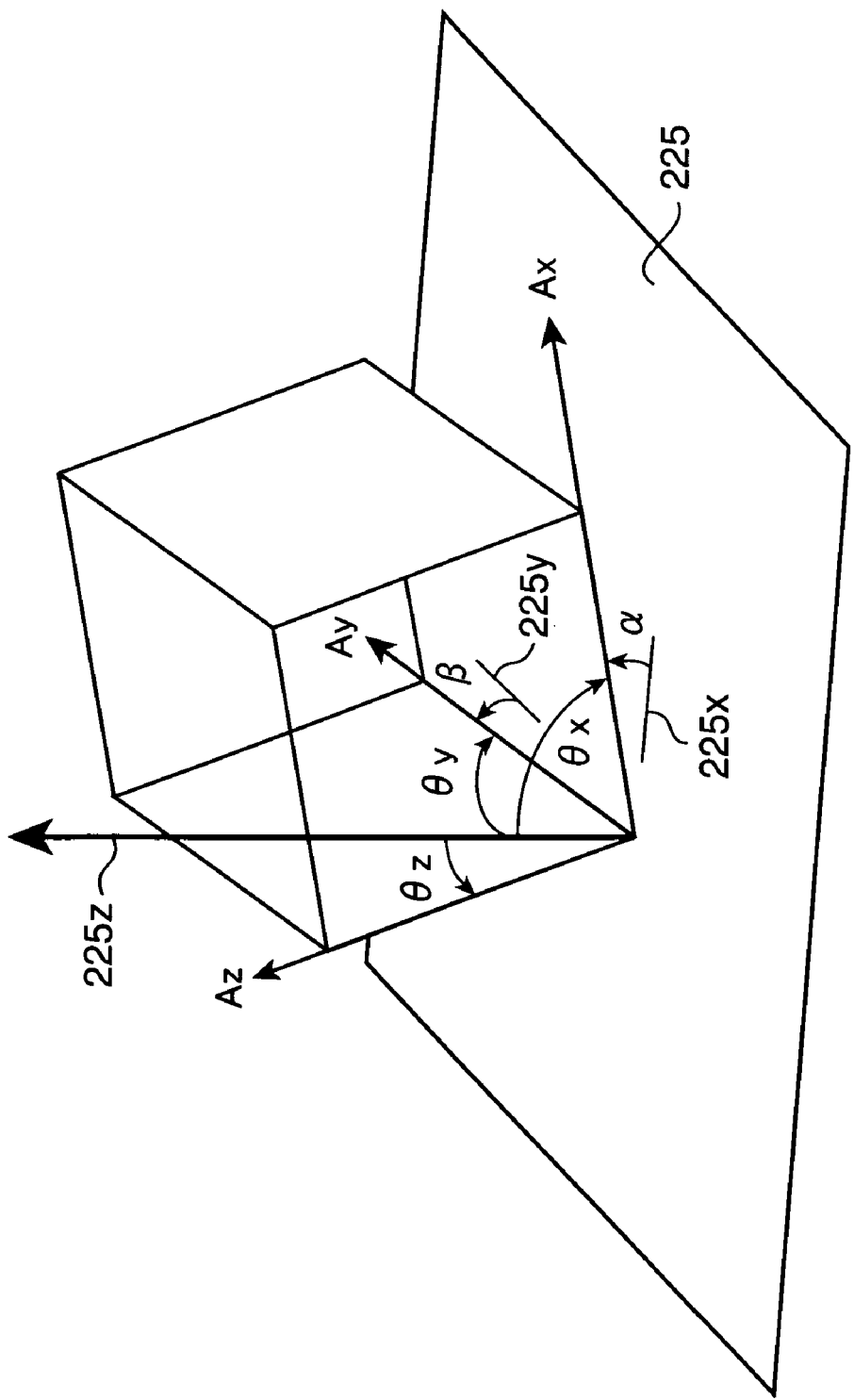
FIG. 7 is a diagram for explaining a principle as to how tilt angles of X-axis, Y-axis, and Z-axis are defined in expressing the position of the acceleration sensor.

FIG. 7 is a diagram for defining angles of the X-axis, Y-axis, and Z-axis with respect to the vertical axis in expressing the position of the acceleration sensor 22. Generally, it is proper to express the position of the sensor in terms of angles of the respective axes with respect to the vertical axis. However, in the case where the sensor is in a normal position where the Z-axis coincides with the vertical axis 225z, it is practical to use an angle α defined by the X-axis Ax and a reference line 225x on an imaginary horizontal plane 225, and an angle β defined by the Y-axis Ay and a reference line 225y on the horizontal plane 225, in place of using an angle θx defined by the X-axis Ax and the vertical axis 225z, and an angle θy defined by the Y-axis Ay and the vertical axis 225z, as shown in FIG. 7, to express a tilt of the sensor relative to the normal position. The upward direction on the horizontal plane 225 in FIG. 7 is positive. In view of this, the angles α, β are used to define the tilt of the X-axis Ax and the tilt of the Y-axis Ay with respect to the horizontal plane 225, and the angle θz is used to define the tilt of the Z-axis Az with respect to the vertical axis 225z to express the tilt of the acceleration sensor 22. Using this definition, when the acceleration sensor 22 is not tilted, i.e. the Z-axis Az coincides with the vertical axis 225z, the angles α, β, and θz are all zero, namely, 0G is outputted from the acceleration sensor 22 with respect to the X-axis, Y-axis, and Z-axis.

Specifically, output values Vx, Vy, and Vz with respect to the X-axis, Y-axis, and Z-axis are obtained by implementing the equations (5), (6), and (7) with use of the angles α, β, and θz, respectively.

$$Vx=X0+Xs\cdot\sin\alpha \quad (5)$$

$$Vy=Y0+Ys\cdot\sin\beta \quad (6)$$

$$Vz=Z0+Zs\cdot\cos\theta z \quad (7)$$

where X0, Y0, and Z0 are correction amounts to be added in the respective equations (5), (6), and (7) to cancel initial displacement of the acceleration sensor 22 with respect to the vertical axis. These correction amounts are added to correct an error resulting from positional displacement of the Z-axis of the acceleration sensor 22 with respect to the vertical axis of the oximeter body 200. Also, Xs, Ys, and Zs represent sensitivities of the acceleration sensor 22 with respect to the X-, Y-, and Z- axes, i.e., count values of outputs from the acceleration sensor 22 with respect to the X-, Y-, and Z-axes per 1G, which are constants, respectively.

A relation is defined as expressed by the equation (8) regarding tilt angles of the three axes with respect to the vertical axis. Obtaining two of the tilt angles in the equation (8) enables to obtain the remaining one of the tilt angles.

$$\sin^2\alpha+\sin^2\beta+\cos^2\theta z=1 \quad (8)$$

Figure 8:
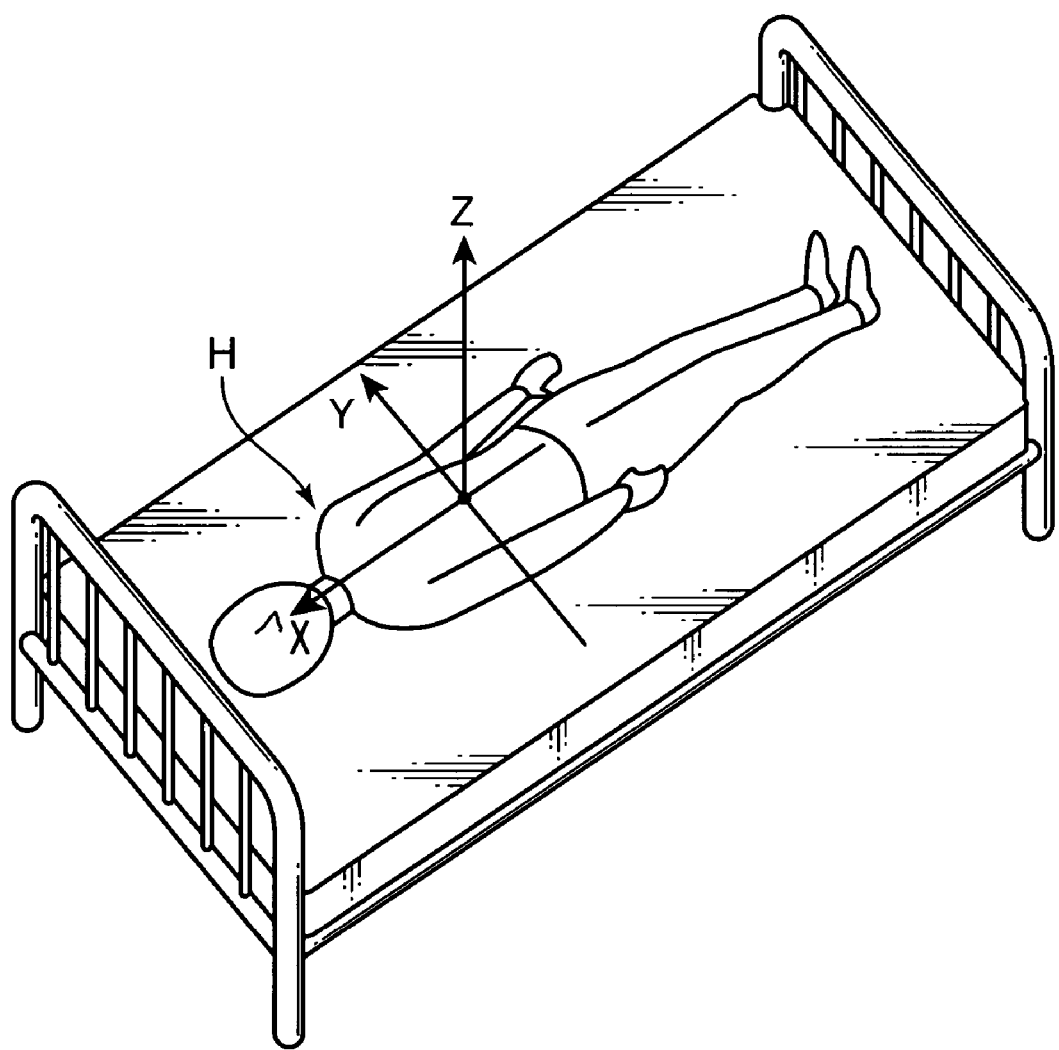
FIG. 8 is a perspective view showing a correlation between the X-axis, Y-axis, and Z-axis of the acceleration sensor shown in FIG. 7, and a lying position of a subject.

The three-axis acceleration sensor 22 may be provided in the oximeter body 200 so that the respective axes of the acceleration sensor 22 coincide with X-, Y-, and Z-axes shown in FIG. 8 for instance in association with a lying position of the subject H. Specifically, in the case where the oximeter body 200 is attached to the body trunk portion of the subject H in a supine position in the manner as shown in FIG. 2, the acceleration sensor 22 is built in the oximeter body 200, with the X-axis corresponding to a second axis of the acceleration sensor 22 extending in a longitudinal direction of the subject's body, the Y-axis corresponding to a first axis of the acceleration sensor 22 extending in a sideways direction of the subject's body, and the Z-axis corresponding to a third axis of the acceleration sensor 22 extending in a depthwise direction of the subject's body.

In the above state, when the subject H makes a movement around the Y-axis, the acceleration sensor 22 detects whether the subject H is in a seated position, in other words, whether the subject H is in a standing position or in a lying position, based on a tilt angle of the X-axis i.e. an output value from the acceleration sensor 22 with respect to the X-axis. Also, in the case where the subject H rolls over around the X-axis, the acceleration sensor 22 detects a body angle of the subject H i.e. the position of the subject H based on a tilt angle of the Y-axis i.e. an output value from the acceleration sensor 22 with respect to the Y-axis. Further, the acceleration sensor 22 detects whether the subject H is in a supine position or a prone position based on the symbol (plus or minus) of the tilt angle of the Z-axis i.e. an output value from the acceleration sensor 22 with respect to the Z-axis.

Next, description is made as to how the body position of the subject H is detected based on the output values from the acceleration sensor 22 with respect to the X-, Y-, and Z- axes. First, the output value from the acceleration sensor 22 with respect to the X-axis is used to detect whether the subject H is in a seated position. Assuming that Px is a count value of the output from the acceleration sensor 22 with respect to the X-axis after A/D conversion, the count value Px is obtained by implementing the equation (9) based on the equation (5).

$$Px = Px0 + Pxs \cdot \sin \alpha \qquad (9)$$

where Px0 is a count value of the correction amount X0 after A/D conversion; and Pxs is a count value (constant) of the output from the acceleration sensor 22 with respect to the X-axis per 1G after A/D conversion.

The tilt angle α of the X-axis can be obtained by implementing the equation (10). When α≧45°, it is judged that the subject H is in a seated position, and when α<45°, it is judged that the subject H is in a lying position.

$$\alpha = \sin^{-1}\left[\frac{P_x - P_{x0}}{P_{xS}}\right] \qquad (10)$$

Subsequently, the output value from the acceleration sensor 22 with respect to the Y-axis is used to detect the body angle of the subject H. Assuming that Py is a count value of the output from the acceleration sensor 22 with respect to the Y-axis after A/D conversion, the count value Py is obtained by implementing the equation (11) based on the equation (6).

$$Py = Py0 + Pys \cdot \sin \beta \qquad (11)$$

where Py0 is a count value of the correction amount Y0 after A/D conversion, and Pys is a count value (constant) of the output from the acceleration sensor 22 with respect to the Y-axis per 1G after A/D conversion.

The tilt angle β of the Y-axis can be obtained by implementing the equation (12). In the equation (12), the angle β is 180° or less.

$$\beta = \sin^{-1}\left[\frac{P_y - P_{y0}}{P_{yS}}\right] \qquad (12)$$

In implementing the equation (12), two cases satisfy the equation: Py−Py0=0, namely, a case where β=0°, which corresponds to a supine position, and a case where β=180°, which corresponds to a prone position. The count value of the output from the acceleration sensor 22 with respect to the Z-axis is used to judge whether the computation results represents a supine position or a prone position. Specifically, when β=0°, θz=0°. Accordingly, the count value of the output from the acceleration sensor 22 with respect to the Z-axis is positive i.e. a count value per +1G. On the other hand, when β=180°, θz=180°. Accordingly, the count value of the output from the acceleration sensor 22 with respect to the Z-axis is negative i.e. a count value per −1G. This enables to make a judgment as to whether the computation results represents a supine position or a prone position.

The tilt angle of the Z-axis can be also obtained by the following approach. Assuming that Pz is a count value of the output from the acceleration sensor 22 with respect to the Z-axis after A/D conversion, the count value Pz is obtained by implementing the equation (13).

$$Pz = Pz0 = Pzs \cdot \cos \theta z \qquad (13)$$

where Pz0 is a count value of the correction amount Z0 after A/D conversion, and Pzs is a count value (constant) of the output from the acceleration sensor 22 with respect to the Z-axis per 1G after A/D conversion.

The tilt angle θz of the Z-axis can be obtained by implementing the equation (14).

$$\theta_z = \cos^{-1}\left[\frac{P_z - P_{z0}}{P_{zS}}\right] \qquad (14)$$

Figure 9:
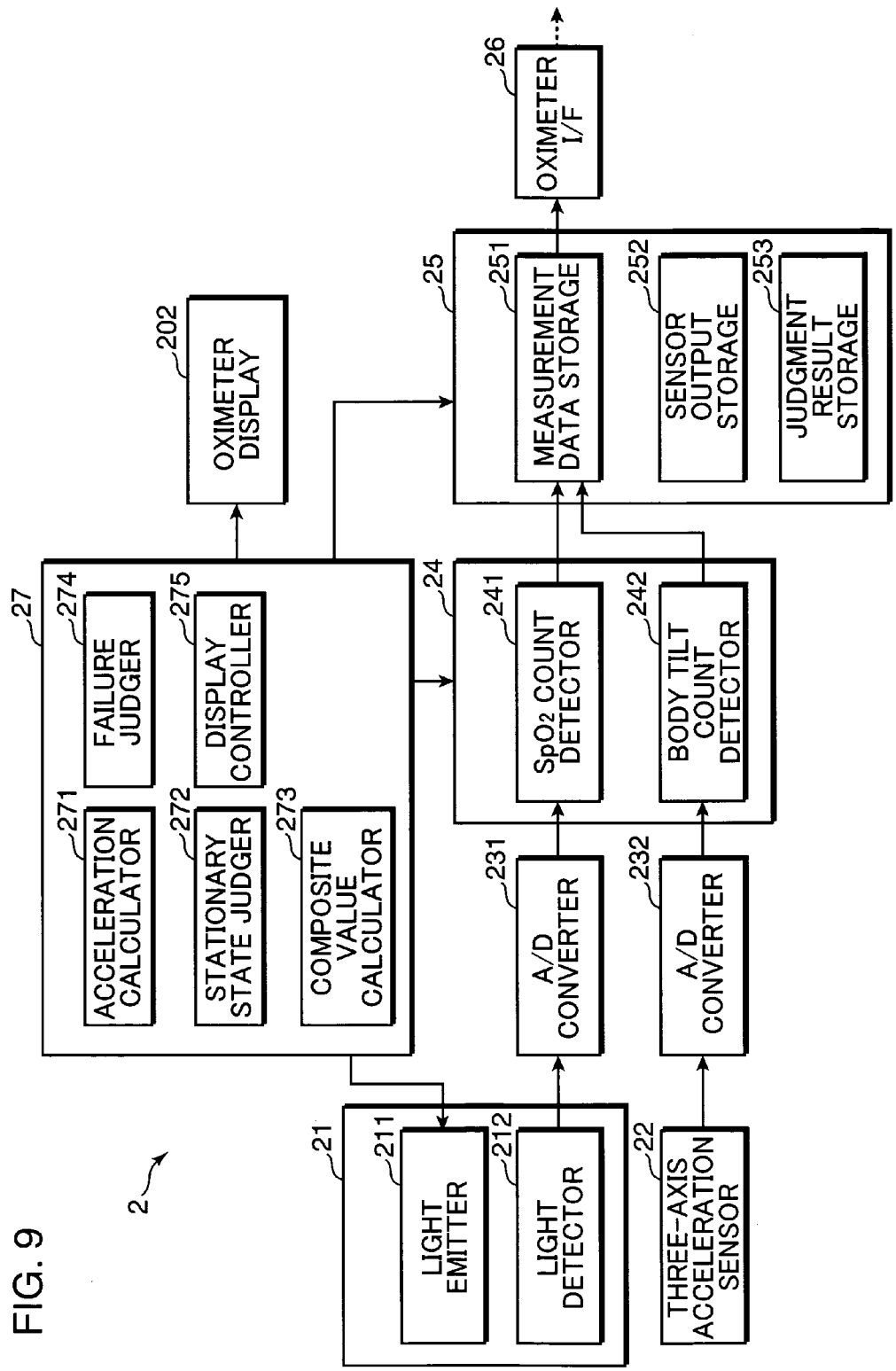
FIG. 9 is a block diagram showing an arrangement of electrical functions of the pulse oximeter.

FIG. 9 is a block diagram of an arrangement showing electrical functions of the pulse oximeter 2. The pulse oximeter 2 includes a first A/D converter 231, a second A/D converter 232, an oximeter calculator 24, a memory 25 as a storage, an oximeter controller 27, and an oximeter interface (I/F) 26 in addition to the oximeter display 202, the probe 21 as a blood oxygen saturation measuring device, and the three-axis acceleration sensor 22 as a body tilt detector.

As mentioned above, the probe 21 has the light emitter 211 and the light detector 212 to acquire measurement data concerning the blood oxygen saturation of the subject. Also, the three-axis acceleration sensor 22 acquires measurement data concerning the body angle of the subject.

An analog current signal outputted from the light detector 212 at a predetermined sampling frequency in accordance with the transmitted amounts of red light and infrared light is converted into a voltage signal by a current/voltage converting circuit (not shown), and the voltage signal is converted into a digital signal by the first A/D converter 231. Similarly, respective output values i.e. analog current signals from the three-axis acceleration sensor 22 with respect to the X-, Y-, and Z-axes are converted into voltage signals corresponding to the aforementioned output values Vx, Vy, and Vz, and then these voltage signals are converted into digital signals by the second A/D converter 232.

The oximeter calculator 24 is a functioning part for obtaining count values corresponding to blood oxygen saturation ($SpO_2$) and body angle based on the digital measurement signals outputted from the first A/D converter 231 and from the second A/D converter 232, respectively. The oximeter calculator 24 includes an $SpO_2$ count detector 241, and a body tilt count detector 242.

The $SpO_2$ count detector 241 detects a count value corresponding to $SpO_2$ every predetermined cycle e.g. every one second in response to receiving the digital measurement signal from the first A/D converter 231 at a fixed interval. The body tilt count detector 242 detects count values corresponding to respective tilts of the X-, Y-, and Z-axes i.e. the aforementioned Px, Py, and Pz every predetermined cycle in response to receiving the digital measurement signal from the second A/D converter 232 at a fixed interval.

The memory 25 includes e.g. a RAM or a like device, and has a measurement data storage 251. The measurement data storage 251 temporarily stores the measurement data acquired by the probe 21 and by the three-axis acceleration sensor 22 i.e. the count values corresponding to the respective measurement data in association with the time when the respective data have been acquired.

The oximeter I/F 26 is an interface, such as RS-232C, USB, or IrDA, to connect the PC 3 and the pulse oximeter 2 for data communication. Specifically, the oximeter I/F 26 functions as an interface for downloading the count values corresponding to the measurement data stored in the memory 25 of the pulse oximeter 2 to the PC 3.

The oximeter controller 27 controls sensing operations by the probe 21 i.e. the light emitter 211 and the light detector 212, and by the three-axis acceleration sensor 22, an operation of calculating the count values by the oximeter calculator 24, and an operation of writing the count values into the memory 25. Specifically, the oximeter controller 27 causes the probe 21 and the three-axis acceleration sensor 22 to acquire the measurement data concerning $SpO_2$ and body angle of the subject at the predetermined sampling frequency, causes the oximeter calculator 24 to calculate the respective count values corresponding to the measurement data, and causes the memory 25 to store the obtained count values therein.

An impact may be applied to the pulse oximeter 2 when the pulse oximeter 2 is inadvertently dropped, for instance, in light of portability of the pulse oximeter 2. The three-axis acceleration sensor 22 may fail to operate properly if an acceleration over a rated value e.g. from 1,000G to 2,000G is applied to the pulse oximeter 2. The operation failure of the three-axis acceleration sensor 22 may give rise to a large detection error concerning a ratio (hereinafter, called as "sensitivity") of an output voltage of the three-axis acceleration sensor 22 when an acceleration is applied thereto, to a reference voltage (hereinafter, called as "offset voltage") of the acceleration sensor 22 under an acceleration of 0G, or generate an abnormal value.

To avoid the above drawbacks, the oximeter controller 27 functionally includes, in addition to the above functioning parts, an acceleration calculator 271, a stationary state judger 272, a composite value calculator 273, a failure judger 274, and a display controller 275.

The acceleration calculator 271 calculates an acceleration Ai based on a voltage Vi when the three-axis acceleration sensor 22 is normally operated by implementing the equation (15) where Vi(+1G) and Vi(−1G) are output values from the three-axis acceleration sensor 22 under a condition that an acceleration of 1G is applied to the three-axis acceleration sensor 22 in plus and minus directions with respect to the respective sensitivity axes. The acceleration calculator 271 corresponds to an acceleration calculator of the invention.

$$Ai = \left(Vi - \frac{Vi(+1G) + Vi(-1G)}{2}\right) / \left(\frac{Vi(+1G) - Vi(-1G)}{2}\right) \quad (15)$$

$(i = x, y, z)$

The stationary state judger 272 judges whether the pulse oximeter 2 i.e. the three-axis acceleration sensor 22 is in a stationary state. The stationary state judger 272 corresponds to a first judger of the invention.

The judgment by the stationary state judger 272 is made based on a judgment as to whether an acceleration calculated based on the output from the three-axis acceleration sensor 22 lies in a predetermined range e.g. from 2 least significant bits (LSB) to 3 LSB or 0.02G to 0.03G during a predetermined judgment duration e.g. 5 seconds.

Figure 10A:
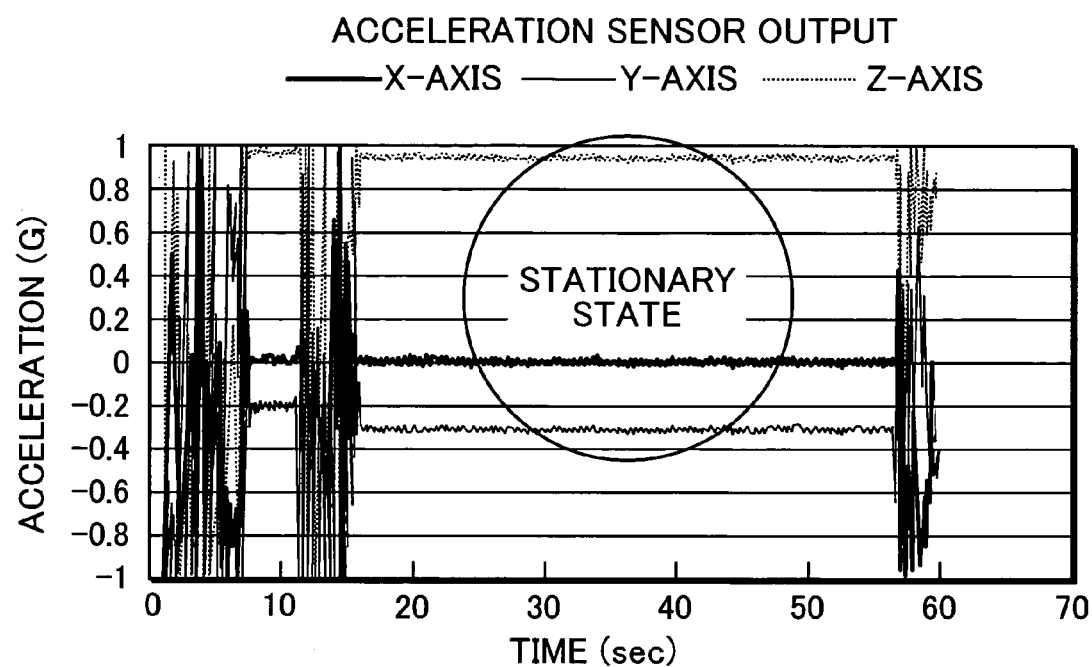
FIG. 10A is a graph showing outputs i.e. computed accelerations from the three-axis acceleration sensor with respect to the X-axis, Y-axis, and Z-axis in the case where the pulse oximeter i.e. the acceleration sensor is in a stationary state.

FIG. 10A is a graph showing an output i.e. a computed acceleration from the three-axis acceleration sensor 22 in the case where the pulse oximeter 2 is in a stationary state. The graph shows examples that an output from the sensor 22 with respect to the X-axis is substantially 0G, an output from the sensor 22 with respect to the Y-axis is substantially −0.3G, and an output from the sensor 22 with respect to the Z-axis is substantially +0.95G when the pulse oximeter 2 is in a stationary state.

Figure 11A:
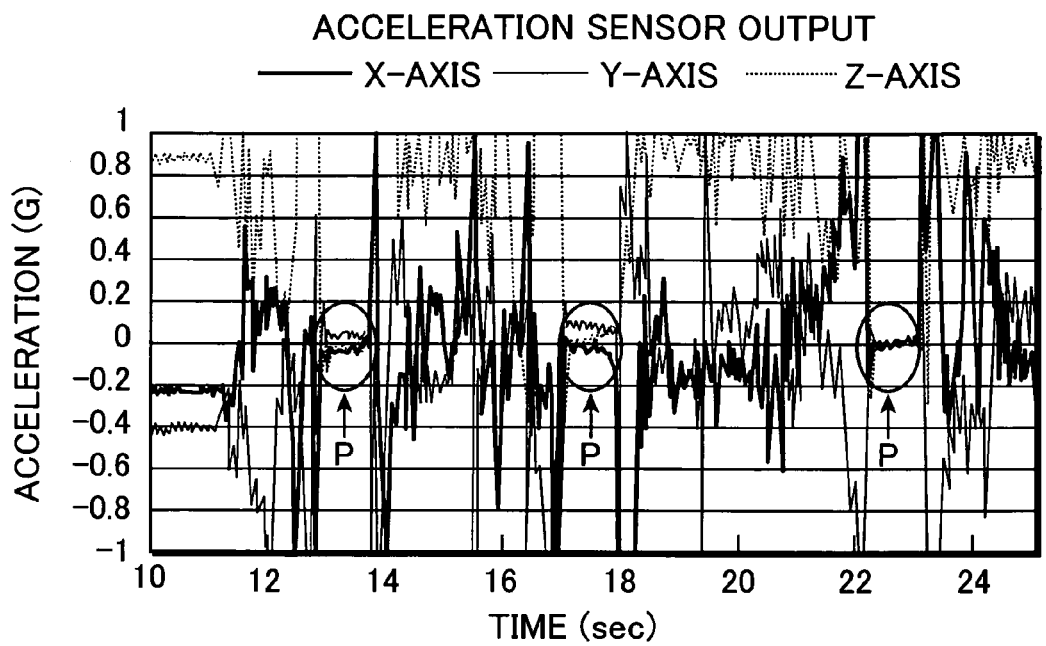
FIG. 11A is a graph showing outputs i.e. computed accelerations from the three-axis acceleration sensor with respect to the X-axis, Y-axis, and Z-axis in the case where the pulse oximeter i.e. the acceleration sensor is in a freefall state.

Theoretically, there is likelihood that an output from the three-axis acceleration sensor 22 may lie in the predetermined range during freefall or an accelerated motion of the oximeter body 200, a uniform rotary motion of the oximeter body 200 around the acceleration sensor 22, or an equivalent motion. FIG. 11A is a graph showing an output i.e. a computed acceleration from the three-axis acceleration sensor 22 when the pulse oximeter 2 is in a freefall state. The graph shows that all the outputs from the acceleration sensor 22 with respect to the X-, Y-, and Z-axes are approximate to zero, as shown by the arrows "P", when the pulse oximeter 2 is in a freefall state.

Actually, however, the freefall involves a small rotary motion. Also, small vibrations are added during the accelerated motion or the uniform rotary motion of the pulse oximeter 2. Accordingly, there is no or less likelihood that all the outputs from the acceleration sensor 22 with respect to the X-, Y-, and Z-axes are zero during the freefall.

Also, appropriately setting the sampling frequency, the judgment duration, and the value of LSB allows for accurate judgment as to whether the pulse oximeter 2 is in a stationary state. For instance, under the condition that the sampling frequency is in the range of 30 to 40 Hz, with an acceleration in the range of 2 to 3 LSB for 5 seconds, an object in freefall would fall by the distance of 122.5 m during the five seconds, and the object, if it is thrown up into the air, would reach the height of 30 m from the ground within the five seconds. It is least likely that the pulse oximeter 2 would be possibly used in such an extreme way as mentioned above. Accordingly performing the judgment operation under the above requirements enables to accurately judge whether the pulse oximeter 2 is in a stationary state.

The composite value calculator 273 calculates a composite value "A", which will be described later, if the stationary state judger 272 judges that the pulse oximeter 2 is in a stationary state. The composite value calculator 273 corresponds to a composite value calculator of the invention.

Assuming that accelerations acting on the X-, Y-, and Z-axes are Ax, Ay, and Az, and a magnitude of a composite vector (hereinafter, called as "composite value A") of the accelerations is "A", the composite value "A" is expressed by the equation (16) using the accelerations Ax, Ay, and Az.

$$A = \sqrt{Ax^2 + Ay^2 + Az^2} \quad (16)$$

Here, the gravitational acceleration acting on the three-axis acceleration sensor 22 is 1G when the three-axis acceleration sensor 22 is in a stationary state. Accordingly, the composite value "A" is expressed by the equation (17).

$$A = G = \sqrt{Gx^2 + Gy^2 + Gz^2} \quad (17)$$

The failure judger 274 judges whether the composite value "A" is out of a predetermined allowable range in response to calculation of the composite value "A" by the composite value calculator 273 so as to determine whether a failure has occurred in the three-axis acceleration sensor 22. The failure judger 274 corresponds to a second judger of the invention.

There is a possibility that the three-axis acceleration sensor 22 in a normal operation state may generate a detection error of ±30 mV in median of offset voltage, and detect sensitivity in the range from 313 to 353 mV under the condition that an output from the three-axis accelerations sensor 22 with a gravitational acceleration of 1G is in the range from 300 to 400 mV, and a characteristic of the A/D converter 232 is 3V/10bit. In such a case, an expected range of the composite value "A" is from 0.78 to 1.22G.

The failure judger 274 judges whether the composite value "A" calculated based on the equation (17) lies in the expected range of the composite value "A" when the pulse oximeter 2 is in a stationary state. Also, the failure nudger 274 determines that a failure has occurred in the three-axis acceleration sensor 22 when the judgment that the calculated composite value "A" has transgressed the expected range is made a predetermined number of times (in this embodiment, twice). For instance, in this example, if a judgment that the composite value "A" calculated based on the output from the three-axis acceleration sensor 22 has transgressed the range of 0.78 to 1.22 G is made twice, the failure judger 274 determines that a failure has occurred in the three-axis acceleration sensor 22.

Figure 10B:
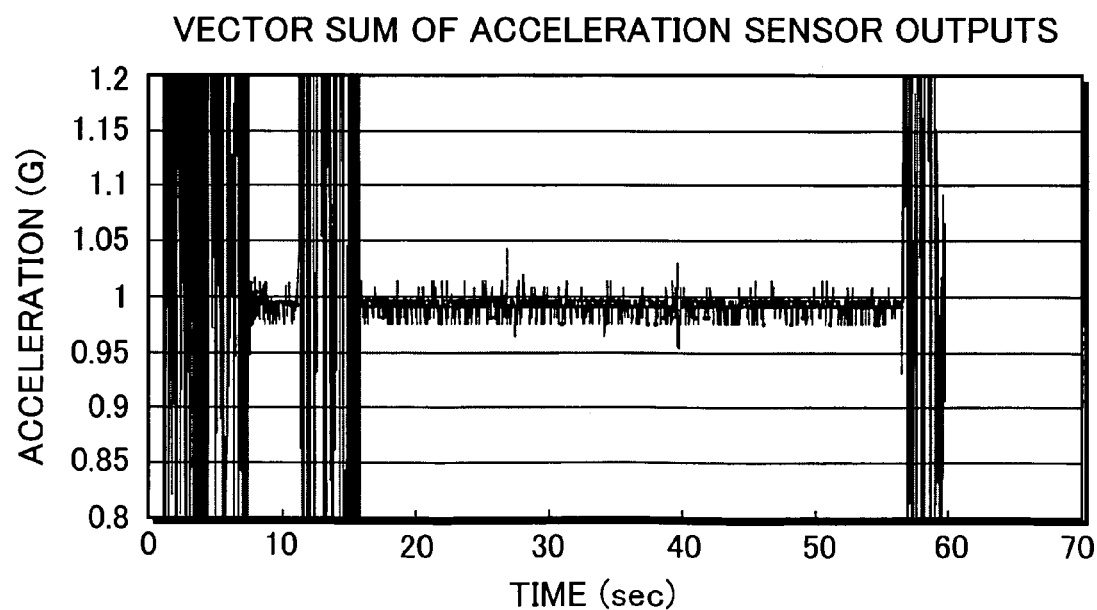
FIG. 10B is a graph showing a composite value of the outputs from the acceleration sensor shown in FIG. 10A.
Figure 11B:
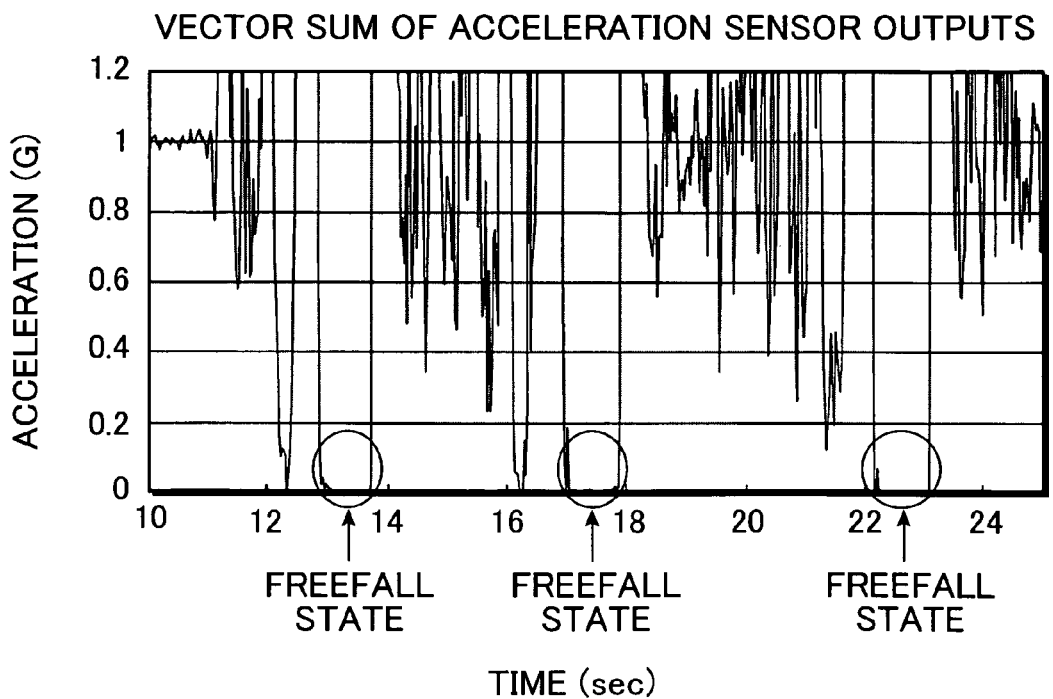
FIG. 11B is a graph showing a composite value of the outputs from the acceleration sensor shown in FIG. 11A.

FIG. 10B is a diagram showing a composite value of outputs from the three-axis acceleration sensor 22 shown in FIG. 10A. FIG. 10B shows that the composite value "A" in a stationary state of the pulse oximeter 2 is approximate to the gravitational acceleration "G". FIG. 11B is a graph showing composite values of outputs from the three-axis acceleration sensor 22 shown in FIG. 11A. FIG. 11B shows that the composite values "A" at the time of freefall of the pulse oximeter 2 are approximate to zero.

The display controller 275 displays, on the oximeter display 202, a judgment result made by the failure judger 274 by way of a message such as "FAILURE OCCURRED", certain characters or the like. The display controller 275 and the oximeter display 202 constitute a display section of the invention.

The memory 25 includes, in addition to the measurement data storage 251, a sensor output storage 252, and a judgment result storage 253. The sensor output storage 252 stores therein output values Vi(+1G) and Vi(−1G) from the three-axis acceleration sensor 22 when an acceleration of 1 G is applied to the three-axis acceleration sensor 22 in plus and minus directions with respect to the respective sensitivity axes under the condition that the three-axis acceleration sensor 22 is operated normally. The output values Vi(+1G) and Vi(−1G) are stored in the memory 25 at the time of shipment of the pulse oximeter 2, for example. The judgment result storage 253 stores therein judgment results made by the failure judger 274. The sensor output storage 252 corresponds to a second storage of the invention, and the judgment result storage 253 corresponds to a first storage of the invention.

Figure 12:
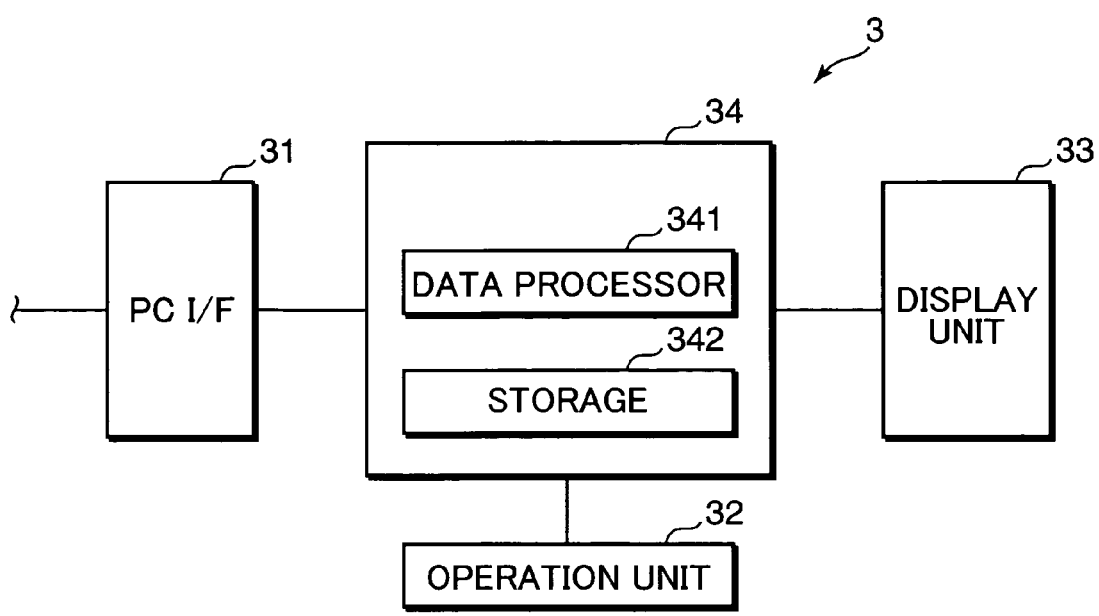
FIG. 12 is a block diagram showing an arrangement of electrical functions of a personal computer.

FIG. 12 is a block diagram showing an arrangement of electrical functions of the PC 3. As shown in FIG. 12, the PC 3 includes a PC I/F 31, a display unit 33, an operation unit 32, and a PC controller 34. The operation unit 32 and the display unit 33 in FIG. 12 corresponds to the operation unit 32 and the display unit 33 in FIG. 1. The PC 3 is an example of a data processor of the invention.

The PC I/F 31 is an interface such as RS-232C, USB, or IrDA, and is an interface for enabling communication between the PC 3 and the pulse oximeter 2.

The PC controller 34 includes a microcomputer, and controls driving of various sections in the PC 3 in association with each other. The PC controller 34 functionally includes a data processor 341 and a storage 342.

The data processor 341 computes the number of times when SpO$_2$ is lowered due to apnea of the subject, based on count value data corresponding to the SpO$_2$ that has been acquired from the pulse oximeter 2 via the PC I/F 31.

The storage 342 includes a RAM for temporarily storing measurement data downloaded from the memory 25 of the pulse oximeter 2, and various data obtained in the relevant sections of the PC main body 30; and a ROM for storing an operation program for operating the PC 3 i.e. the living body information measurement system 1, and the like.

Figure 13:
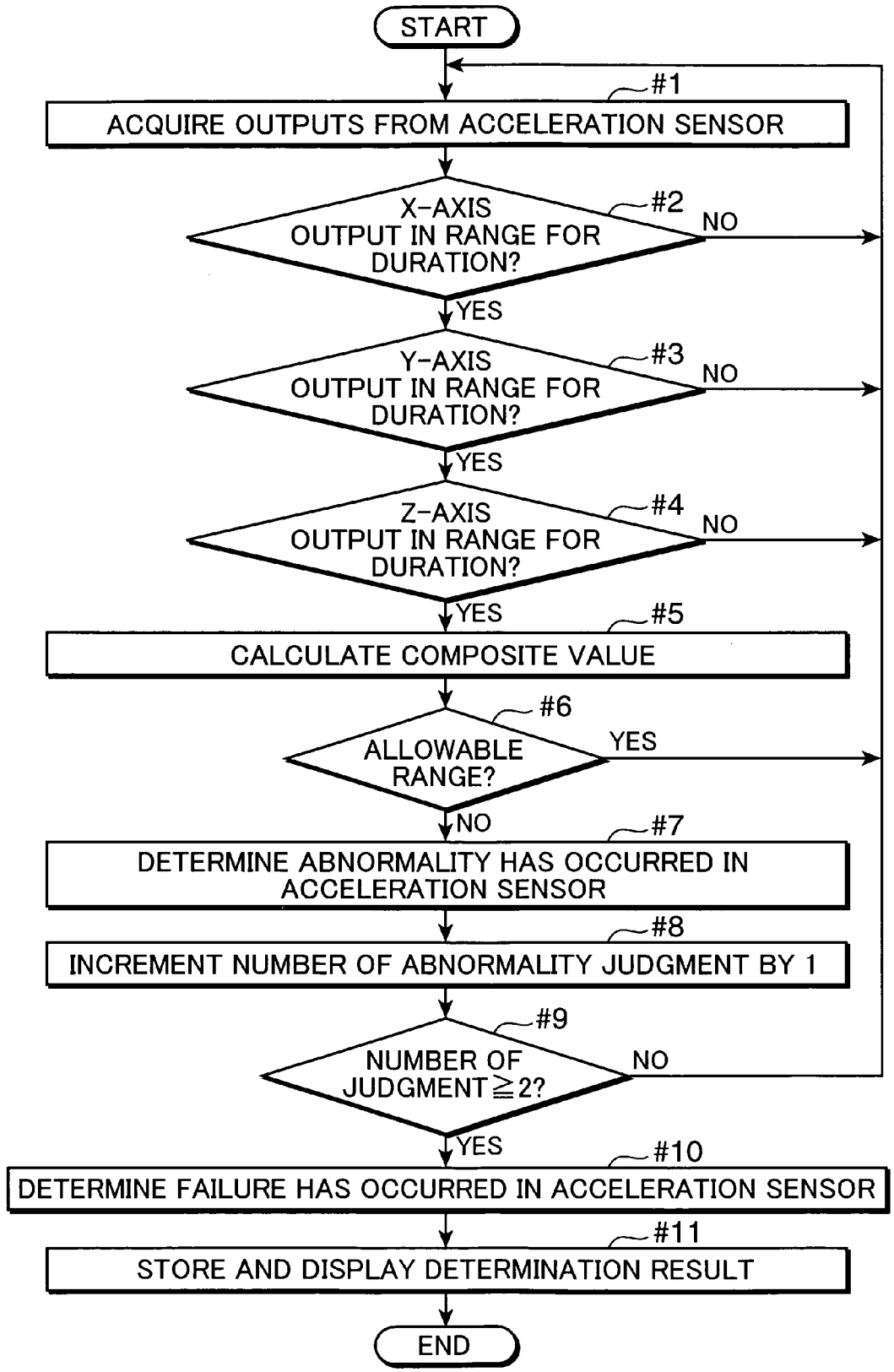
FIG. 13 is a flowchart showing a failure diagnosis to be executed by the pulse oximeter.

FIG. 13 is a flowchart showing a failure diagnosis to be executed by the pulse oximeter 2. When the oximeter controller 27 acquires outputs from the three-axis acceleration sensor 22 (Step #1), the oximeter controller 27 judges whether accelerations calculated based on the outputs from the three-axis acceleration sensor 22 with respect to the X-, Y-, and Z-axes lie within a predetermined range e.g. from 2 LSB to 3 LSB or from 0.02G to 0.03G for a predetermined duration e.g. 5 seconds (Steps #2 through #4). If the judgment results show that all the accelerations with respect to the X-, Y-, and Z-axes are out of the range for the duration (NO in Steps #2, #3, or #4), the oximeter controller 27 judges that the pulse oximeter 2 is not in a stationary state, and the routine returns to the operation in Step #1.

If, on the other hand, the oximeter controller 27 judges that the outputs lie within the predetermined range for the duration (YES in Steps #2, #3, and #4), the oximeter controller 27 judges that the pulse oximeter 2 is in a stationary state, and computes a composite value "A" of the accelerations acquired based on the outputs from the three-axis acceleration sensor 22 with respect to the X-, Y-, and Z-axes, using the equation (16) (Step #5).

The oximeter controller 27, then, judges whether the composite value "A" lies in a predetermined range e.g. from 0.78 to 1.22G (Step #6). If the composite value "A" lies within the predetermined range (YES in Step #6), the oximeter controller 27 determines that no failure has occurred in the acceleration sensor 22, and the routine returns to the operation in Step #1. If, on the other hand, the composite value "A" transgresses the predetermined range (NO in Step #6), the oximeter controller 27 judges that the composite value "A" represents abnormality (Step #7), and increments the number of abnormality judgments by one (Step #8).

Subsequently, the oximeter controller 27 judges whether the number of abnormality judgments has reached twice (Step #9). If the oximeter controller 27 judges that the number of abnormality judgments has not reached twice (NO in Step #9), the routine returns to the operation in Step #1. If, on the other hand, the oximeter controller 27 judges that the number of abnormality judgments has reached twice (YES in Step #9), the oximeter controller 27 determines that a failure has occurred in the acceleration sensor 22 (Step #10), stores the determination result in the memory 25, and displays, on the oximeter display 202, a message indicating that a failure has occurred (Step #11).

In this way, a diagnosis is made as to whether a detection failure has occurred in the three-axis acceleration sensor 22, using the outputs from the three-axis acceleration sensor 22, which is an object for failure diagnosis. This eliminates the need of providing plural acceleration sensors as required in the conventional art, or providing another sensor in addition to the three-axis acceleration sensor 22. Thus, the arrangement contributes to cost reduction and miniaturization of the pulse oximeter 2, as compared with the conventional art.

Also, since a failure determination is automated, the user of the pulse oximeter 2 is free from a burden of manually calibrating an output from the three-axis acceleration sensor 22, which contributes to improved operability of the pulse oximeter 2.

Further, since the judgment result on detection failure is displayed on the oximeter display 202, the user of the pulse oximeter 2 can confirm the judgment result promptly. As a result, there is no likelihood that the user may use the pulse oximeter 2 without knowing that a failure has occurred in the three-axis acceleration sensor 22, thereby preventing a living body analysis based on erroneous data.

The invention may include the following modifications (1) through (4) in addition to or in place of the foregoing embodiment.

(1) In the embodiment, a failure determination is made in the pulse oximeter 2. Alternatively, one or more of the stationary state judger 272, the composite value calculator 273, and the failure judger 274 may be provided in the PC 3, and data may be communicated between the PC 3 and the pulse oximeter 2 according to needs, for instance.

Also, the PC 3 may be provided with the display controller 275 so that the display controller 275 controls the display unit 33 of the PC 3 to display a failure detection result on the display unit 33. Alternatively, the display controller 275 may issue a command to the pulse oximeter 2 so as to display the failure detection result on the oximeter display 202.

(2) The parameters used in judging that the pulse oximeter 2 is in a stationary state may be other than the ones shown in the embodiment, i.e., the judgment duration of 5 seconds, the range of acceleration computed based on the outputs from the acceleration sensor 22, from 2 LSB to 3 LSB or 0.02 G to 0.03G. The parameters can be arbitrarily set.

(3) In the embodiment, after the judgment that the outputs from the three-axis acceleration sensor 22 with respect to the three axes show a stationary state of the pulse oximeter 2, a composite value "A" of the accelerations is calculated, and a failure diagnosis is made by judging whether the composite value "A" lies within the predetermined range. Alternatively, the composite value of the accelerations may be used to determine whether the pulse oximeter 2 is in a stationary state. In the altered arrangement, a failure diagnosis is made by judging that the pulse oximeter 2 is in a stationary state if the composite value "A" lies within a predetermined range e.g. (an average acceleration ±0.05G) for a predetermined duration e.g. 5 seconds, and by determining that a failure has occurred in the acceleration sensor 22 if the composite value "A" has transgressed an allowable range e.g. from 0.78G to 1.22G.

(4) The invention is not only applied to the pulse oximeter, but also applied to electronic devices in general. The invention has particularly advantageous effects if the invention is applied to a portable electronic device having a high probability that an impact may be applied to the electronic device by dropping or the like.

The aforementioned embodiment primarily includes the following.

A failure diagnostic device according to an aspect of the invention is a failure diagnostic device for diagnosing whether a failure has occurred in an acceleration sensor to be loaded in an electronic device. The failure diagnostic device comprises: an acceleration calculator for calculating an acceleration applied to the electronic device based on an output from the acceleration sensor; and a first judger for judging whether the electronic device is in a stationary state based on a judgment as to whether an output value from the acceleration calculator lies in a predetermine range for a predetermined duration.

In the above arrangement, the acceleration calculator calculates the acceleration based on the output from the acceleration sensor, and the first judger judges whether the electronic device is in a stationary state based on the judgment as to whether the output value from the acceleration calculator lies within the predetermined range for the predetermined duration.

Preferably, in the case where the acceleration sensor is provided with respect to each of three axis directions substantially orthogonal to each other, the failure diagnostic device may further comprise: a composite value calculator for calculating a composite value of output values from the respective acceleration sensors in the three axis directions based on a judgment by the first judger that the electronic device is in the stationary state; and a second judger for judging whether the composite value calculated by the composite value calculator lies in a predetermined allowable range to diagnose whether a failure has occurred in the acceleration sensors based on a judgment result on the composite value.

In the above arrangement, upon judgment by the first judger that the electronic device is in the stationary state, the composite value calculator calculates the composite value of the output values from the respective acceleration sensors, and the second judger judges whether the composite value calculated by the composite value calculator lies within the allowable range to diagnose whether a failure has occurred in the acceleration sensors based on the judgment result on the composite value.

The composite value corresponds to a magnitude of a composite vector, which is obtained by synthesizing vectors corresponding to outputs from the respective acceleration sensors under a condition that magnitudes of the outputs from the respective acceleration sensors, and directions of respective accelerations are expressed in terms of a vector. The definition of the composite value in terms of a vector enables to diagnose whether a failure has occurred in the acceleration sensors with use of the outputs themselves from the acceleration sensors.

Preferably, the failure diagnostic device may further comprise a display section for displaying a diagnosis result by the second judger.

In the above arrangement, since the failure diagnostic device has the display section for displaying the diagnosis result as to whether the composite value calculated by the composite value calculator lies within the allowable range, a user of the failure diagnostic device is notified of the diagnosis result through the display section. This prevents measurement or a like operation, with the user being kept being uninformed of abnormality of the acceleration sensor, thereby preventing erroneous control or erroneous phenomena detection by the electronic device based on erroneous measurement data.

Preferably, the failure diagnostic device may further comprise a transmitter for transmitting data concerning a diagnostic result by the second judger to an external device.

In the above arrangement, the failure diagnostic device has the transmitter for transmitting, to the external device, the diagnosis result as to whether the composite value calculated by the composite value calculator lies within the allowable range. This allows the user to execute a certain operation based on the diagnosis result with use of the external device.

Preferably, the failure diagnostic device may further comprise a first storage for storing data concerning a diagnostic result by the second judger.

In the above arrangement, the failure diagnostic device has the first storage for storing the data concerning the diagnosis result as to whether the composite value calculated by the composite value calculator lies within the allowable range. This arrangement enables to readily provide the data concerning the diagnosis result.

In any one of the above arrangements concerning the failure diagnostic device, preferably, the acceleration calculator may calculate an acceleration Ai based on an output value Vi from the acceleration sensor, using the following equation (1), where G is a gravitational acceleration, and Vi(+1G) and Vi(−1G) are output values from the acceleration sensor when an acceleration of 1G and an acceleration of −1G are applied to the electronic device in a normal operation state of the acceleration sensor, respectively:

$$Ai = \left(Vi - \frac{Vi(+1G) + Vi(-1G)}{2}\right) / \left(\frac{Vi(+1G) - Vi(-1G)}{2}\right) \quad (1)$$
$$(i = x, y, z)$$

The above arrangement provides an approach of calculating the acceleration Ai with use of the output Vi itself from the acceleration sensor. In this case, preferably, the output values Vi(+1G) and Vi(−1G) may be pre-stored.

An electronic device according to another aspect of the invention comprises: an acceleration sensor; the failure diagnostic device recited in any one of the above arrangements; and a detector for detecting a movement and/or a tilt of an object to which the electronic device is mounted, using an output from the acceleration sensor.

In the above arrangement, the electronic device provided with the function of detecting the movement and/or the tilt of the object to which the electronic device is mounted, using the output from the acceleration sensor, enables to diagnose whether a failure has occurred in the acceleration sensor using the output itself from the acceleration sensor.

Preferably, the electronic device may further comprise: a first input section for allowing a user to input a command to execute an operation of the failure diagnostic device; and a first controller for controlling the failure diagnostic device to execute the operation in response to receiving the command by the first input section when the detector is in an inoperative state.

In the above arrangement, since the user is allowed to input the command to execute the operation of the failure diagnostic device, the user can perform the failure diagnosis at any time with use of the failure diagnostic device.

Preferably, the electronic device may further comprise: a receiver for receiving, from an external device, command data indicating execution of the operation of the failure diagnostic device; and a second controller for controlling the failure diagnostic device to execute the operation in response to receiving the command data by the receiver when the detector is in an inoperative state.

In the above arrangement, the electronic device has the receiver for receiving, from the external device, the command data indicating execution of the operation of the failure diagnostic device; and the second controller for controlling the failure diagnostic device to execute the operation in response to receiving the command data by the receiver when the detector is in the inoperative state. This allows the user to, for instance, remotely operate the failure diagnostic device i.e. the electronic device with use of the external device.

Preferably, in any one of the above arrangements concerning the electronic device, the electronic device may be a living body information measurement device for acquiring data concerning living body information.

In the above arrangement, the effects of the invention can be advantageously obtained in use of the electronic device, particularly, in use of the living body information measurement device of acquiring data concerning living body information. Examples of the living body information are information on blood oxygen saturation, pulse rate, breathing, electrocardiogram result, blood sugar, and blood pressure.

A failure diagnostic system according to yet another aspect of the invention comprises: an electronic device loaded with an acceleration sensor; and a data processor which is communicable with the electronic device via a communication route. The failure diagnostic system is so configured as to diagnose whether a failure has occurred in the acceleration sensor in cooperation with the electronic device and the data processor, wherein the electronic device includes: the acceleration sensor provided with respect to each of three axis directions substantially orthogonal to each other; an acceleration calculator for calculating accelerations applied to the electronic device with respect to the three axis directions based on outputs from the acceleration sensors; and a transmitter for transmitting, to the data processor, data concerning the accelerations calculated by the acceleration calculator, and the data processor includes: a receiver for receiving the data concerning the accelerations from the transmitter; a first judger for judging whether the electronic device is in a stationary state based on a judgment as to whether an output value indicating the acceleration data received by the receiver lies within a predetermine range for a predetermined duration; a composite value calculator for calculating a composite value of output values from the respective acceleration sensors based on a judgment by the first judger that the electronic device is in the stationary state; and a second judger for judging whether the composite value calculated by the composite value calculator lies within a predetermined allowable range to diagnose whether a failure has occurred in the acceleration sensors based on a judgment result on the composite value.

In the above arrangement, the failure diagnostic system is so configured that the electronic device and the data processor are communicable via the communication route to diagnose whether a failure has occurred in the acceleration sensor loaded in the electronic device in cooperation with each other. This allows for failure diagnosis with use of the output itself from the acceleration sensor.

In the failure diagnostic system, preferably, the electronic device and/or the data processor may further include a display section for displaying a diagnosis result by the second judger.

In the above arrangement, since the electronic device and/or the data processor has the display section for displaying the diagnosis result as to whether the composite value calculated by the composite value calculator lies within the allowable range, the user of the failure diagnostic device is notified of the diagnosis result through the display section. This prevents measurement or a like operation, with the user being kept being uninformed of abnormality of the acceleration sensor, thereby preventing erroneous control or erroneous phenomena detection by the electronic device based on erroneous measurement data.

In the failure diagnostic system, preferably, the electronic device and/or the data processor may further include a storage for storing data concerning a diagnostic result by the second judger. This arrangement enables to readily provide the data concerning the diagnosis result.

In any one of the arrangements concerning the failure diagnostic system, preferably, the electronic device may further include a detector for detecting a movement and/or a tilt of an object to which the electronic device is mounted, using the outputs from the acceleration sensors.

In the above arrangement, the failure diagnostic system includes the electronic device having the function of detecting the movement and/or the tilt of the object to which the electronic device is mounted, using the outputs from the acceleration sensors. This enables to diagnose whether a failure has occurred in the acceleration sensors using the outputs themselves from the acceleration sensors.

In any one of the arrangements concerning the failure diagnostic system, preferably, the electronic device may be a living body information measurement device for acquiring data concerning living body information.

According to the various aspects of the invention, a diagnosis is made as to whether a failure has occurred in the acceleration sensor(s) using the output(s) from the acceleration sensor(s), which is an object for failure diagnosis. This eliminates the need of providing plural acceleration sensors, as required in the conventional art, or providing a reference sensor in addition to the acceleration sensor, which contributes to cost reduction and miniaturization of the electronic device.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A failure diagnostic device for diagnosing whether a failure has occurred in an acceleration sensor included as part of an electronic device, the failure diagnostic device comprising:
   an acceleration calculator for calculating an acceleration of the electronic device based on an output from the acceleration sensor;
   a first judger for judging whether the electronic device is in a stationary state based on a judgment as to whether an output value from the acceleration calculator lies in a predetermined range for a predetermined duration;
   a calculator for calculating a target value based on output values from the acceleration sensor when the first judger judges that the electronic device is in the stationary state; and
   a second judger for judging whether the target value calculated by the calculator lies in a predetermined allowable range to diagnose whether a failure has occurred in the acceleration sensor.

2. The failure diagnostic device according to claim 1, wherein:
   the acceleration sensor includes three acceleration sensors, a respective one of which is provided for each of three axis directions substantially orthogonal to each other;
   said calculator is a composite value calculator for calculating a composite value of output values from the respective acceleration sensors in the three axis directions based on a judgment by the first judger that the electronic device is in the stationary state; and
   said second judger judges whether the composite value calculated by the composite value calculator lies in a predetermined allowable range to diagnose whether a failure has occurred in the respective acceleration sensors based on a judgment result on the composite value.

3. The failure diagnostic device according to claim 2, further comprising:
   a display section for displaying a diagnosis result by the second judger.

4. The failure diagnostic device according to claim 2, further comprising:
   a transmitter for transmitting data concerning a diagnostic result by the second judger to an external device.

5. The failure diagnostic device according to claim 2, further comprising:
   a storage for storing data concerning a diagnostic result by the second judger.

6. The failure diagnostic device according to claim 1, wherein
   the acceleration calculator calculates an acceleration Ai based on an output value Vi from the acceleration sensor, using the following equation (1), where G is a gravitational acceleration, and Vi(+1G) and Vi(−1G) are output values from the acceleration sensor when an acceleration of 1G and an acceleration of -1G are applied to the electronic device in a normal operation state of the acceleration sensor, respectively:

$$Ai = \left(Vi - \frac{Vi(+1G) + Vi(-1G)}{2}\right) \bigg/ \left(\frac{Vi(+1G) - Vi(-1G)}{2}\right) \quad (1)$$

$(i = x, y, z).$

7. The failure diagnostic device according to claim 6, further comprising:
   a storage for storing the output values Vi(+1G) and Vi(−1G) in advance.

8. An electronic device comprising:
   an acceleration sensor;
   a failure diagnostic device for diagnosing whether a failure has occurred in the acceleration sensor; and
   a detector for detecting a movement and/or a tilt of an object to which the electronic device is mounted, using an output from the acceleration sensor, wherein
   the failure diagnostic device includes:
      an acceleration calculator for calculating an acceleration of the electronic device based on the output from the acceleration sensor;
      a first judger for judging whether the electronic device is in a stationary state based on a judgment as to whether an output value from the acceleration calculator lies within a predetermined range for a predetermined duration;
   a calculator for calculating a target value based on output values from the acceleration sensor when the first judger judges that the electronic device is in the stationary state; and
   a second judger for judging whether the target value calculated by the calculator lies in a predetermined allowable range to diagnose whether a failure has occurred in the acceleration sensor.

9. The electronic device according to claim 8, wherein
   the acceleration sensor includes three acceleration sensors, a respective one of which is provided for each of three axis directions substantially orthogonal to each other;
   said calculator is a composite value calculator for calculating a composite value of output values from the respective acceleration sensors in the three axis directions based on a judgment by the first judger that the electronic device is in the stationary state; and
   said second judger judges whether the composite value calculated by the composite value calculator lies in a predetermined allowable range to diagnose whether a failure has occurred in the respective acceleration sensors based on a judgment result on the composite value.

10. The electronic device according to claim 8, wherein
    the electronic device is a living body information measurement device for acquiring data concerning living body information.

11. A failure diagnostic system comprising:
an electronic device loaded with an acceleration sensor; and
a data processor configured to communicate with the electronic device via a communication route, the failure diagnostic system being so configured as to diagnose whether a failure has occurred in the acceleration sensor in cooperation with the electronic device and the data processor, wherein
the electronic device includes:
the acceleration sensor, which includes three acceleration sensors, a respective one of which is provided for each of three axis directions substantially orthogonal to each other;
an acceleration calculator for calculating accelerations of the electronic device with respect to the three axis directions based on outputs from the respective acceleration sensors; and
a transmitter for transmitting, to the data processor, data concerning the accelerations calculated by the acceleration calculator, and
the data processor includes:
a receiver for receiving the data concerning the accelerations from the transmitter;
a first judger for judging whether the electronic device is in a stationary state based on a judgment as to whether an output value indicating the acceleration data received by the receiver lies within a predetermined range for a predetermined duration;
a composite value calculator for calculating a composite value of output values from the respective acceleration sensors based on a judgment by the first judger that the electronic device is in the stationary state; and
a second judger for judging whether the composite value calculated by the composite value calculator lies within a predetermined allowable range to diagnose whether a failure has occurred in the respective acceleration sensors based on a judgment result on the composite value.

12. The failure diagnostic system according to claim 11, further comprising:
a display section, provided in the electronic device and/or the data processor, for displaying a diagnosis result by the second judger.

13. The failure diagnostic system according to claim 11, further comprising:
a storage, provided in the electronic device and/or the data processor, for storing data concerning a diagnostic result by the second judger.

14. The failure diagnostic system according to claim 11, further comprising:
a detector, provided in the electronic device, for detecting a movement and/or a tilt of an object to which the electronic device is mounted, using the outputs from the respective acceleration sensors.

15. The failure diagnostic system according to claim 11, wherein
the electronic device is a living body information measurement device for acquiring data concerning living body information.

16. A failure diagnostic method for diagnosing whether a failure has occurred in an acceleration sensor included as part of an electronic device, the method comprising:
calculating an acceleration of the electronic device based on an output from the acceleration sensor;
judging whether the electronic device is in a stationary state based on a judgment as to whether an output value concerning the acceleration from the acceleration sensor lies within a predetermined range for a predetermined duration;
calculating a target value based on output values from the acceleration sensor when the electronic device is judged to be in the stationary state; and
judging whether the calculated target value lies in a predetermined allowable range to diagnose whether a failure has occurred in the acceleration sensor.

17. The method according to claim 16, the method further comprising:
providing three acceleration sensors, a respective one of which is provided for each of three axis directions substantially orthogonal to each other, as the acceleration sensor; and wherein:
calculating a target value includes calculating a composite value of the output values from the respective acceleration sensors if the electronic device is judged to be in a stationary state; and
judging whether the calculated target value lies in a predetermined allowable range includes judging whether the composite value lies within a predetermined allowable range to diagnose whether a failure has occurred in the respective acceleration sensors based on a judgment result on the composite value.

* * * * *

UNITED STATES PATENT AND TRADEMARK OFFICE
CERTIFICATE OF CORRECTION

PATENT NO.        : 7,600,409 B2  
APPLICATION NO.   : 11/489871  
DATED             : October 13, 2009  
INVENTOR(S)       : Akihiro Ukai It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

Fifth Day of October, 2010

David J. Kappos  
*Director of the United States Patent and Trademark Office*